United States Patent [19]

Okamoto et al.

[11] Patent Number: 5,329,010
[45] Date of Patent: Jul. 12, 1994

[54] QUINONE DERIVATIVES

[75] Inventors: Yasushi Okamoto; Katsuya Tagami; Shigeki Hibi; Hirotoshi Numata; Tetsuya Kawahara; Naoki Kobayashi; Masanobu Shinoda; Koukichi Harada; Kaname Miyamoto; Koichi Abe, all of Ibaraki, Japan

[73] Assignee: Eisai Co., Ltd., Tokyo, Japan

[21] Appl. No.: 840,862

[22] Filed: Feb. 25, 1992

[30] Foreign Application Priority Data

Mar. 11, 1991 [JP] Japan .................. 3-044709
Jul. 18, 1991 [JP] Japan .................. 3-178161

[51] Int. Cl.$^5$ ................ C07D 213/50; C07D 233/64
[52] U.S. Cl. ........................... 546/342; 548/341.5
[58] Field of Search ............ 546/342; 514/277, 399; 548/341.5

[56] References Cited

U.S. PATENT DOCUMENTS 4,851,413  7/1989  Terao et al. .................. 514/277

FOREIGN PATENT DOCUMENTS 2024479  3/1991  Canada .
0092136  10/1983  European Pat. Off. .
0419905  4/1991  European Pat. Off. .

OTHER PUBLICATIONS

Merck Index, 9th edition, 1976, #7770.
*The Pharmacological Basis of Therapeutics*, 8th Edition, Goodman & Gilman, pp. 1196 and 1457, 1990.
Journal of Medicinal Chemistry, vol. 34, No. 1, Jan. 1991, pp. 267-276, Ohkawa et al, "Dual inhibitors of thromboxane A2 synthase and 5-lipoxygenase, etc."
Patent Abstracts of Japan, vol. 9, No. 301 (C-316) Nov. 1985 and JP-A≠40 139 646 (Ootsuka Seiyaki Koujiyou KK) Jul. 24, 1985, Abstract.

*Primary Examiner*—C. Warren Ivy
*Assistant Examiner*—D. Margaret M. Mach
*Attorney, Agent, or Firm*—Flynn, Thiel, Boutell & Tanis

[57] ABSTRACT

The present invention is a quinone derivative which exhibits excellent therapeutic activity represented by the general formula (I) or a pharmacologically acceptable salt thereof:

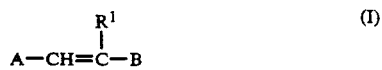

wherein A stands for a group represented by the formula:

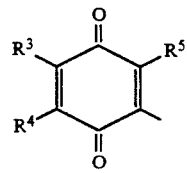

(wherein $R^3$, $R^4$ and $R^5$ is the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are each a lower alkoxy group $R^1$ stands for a heteroarylalkyl group; and B stands for a carboxyl group or a protected carboxyl group.

28 Claims, No Drawings

QUINONE DERIVATIVES

FIELD OF THE INVENTION

The present invention relates to a quinone derivative exhibiting an excellent activity as a drug.

BACKGROUND OF THE INVENTION

Among inflammatory mediators, leukotrienes and thromboxanes have recently been noticed. They each cause inflammation alone or interact with each other to cause it, or participate in the continuation of inflammation. However, few compounds exhibiting both leukotrienes production-inhibiting activity and thromboxanes production-inhibiting activity have been found.

The inventors of the present invention have made intensive studies for many years to obtain a compound exhibiting both of the above-mentioned activities and have found that a quinone derivative which will be described below exhibits both the activities at a well-balanced activity ratio and is excellent as a so-called dual inhibitor. The present invention has been accomplished on the basis of this finding.

SUMMARY OF THE INVENTION

The present invention provides a quinone derivative represented by the following general formula (I) or a pharmacologically acceptable salt thereof:

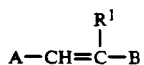

(I)

wherein A stands for a group represented by the formula:

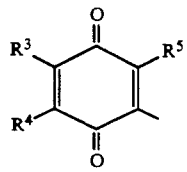

(wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group) or a group represented by the formula:

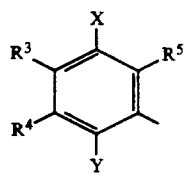

(wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that a case wherein $R^3$ and $R^4$ are each a lower alkoxy group simultaneously is excepted; X and Y are the same or different from each other and each stand for a hydroxyl group or a protected hydroxyl group); $R^1$ stands for a heteroarylalkyl group; and B stands for a carboxyl group or a protected carboxyl group.

Preferably quinone derivatives or pharmacologically acceptable salts thereof of the present invention include derivatives where $R^1$ in the general formula (I) is a heteroarylalkyl group, where $R^3$ in the genaral formula (I) is a lower alkoxy group, where $R^4$ in the general formula (I) is a lower alkyl group, where $R^5$ in the general formula (I) is a lower alkyl group, where X in the general formula (I) is a hydroxy group or a alkoxy group, where Y in the general formula (I) is a hydroxy group or a alkoxy group and where B in the general formula (I) is a carboxyl group.

Still preferably quinone derivatives or pharmacologically acceptable salts thereof of the present invention include derivatives where $R^1$ in the general formula (I) is a pyridylhexyl group or a pyridylpentyl group, where $R^3$ in the general formula (I) is a methoxy group or a methyl group, where $R^4$ in the general formula (I) is a methyl group or a methoxy group, where $R^5$ in the general formula (I) is a methyl group or a methoxy group, where X in the general formula (I) is a hydroxy group or a methoxy group and where Y in the general formula (I) is a hydroxy group or a methoxy group.

The quinone derivative portion of the quinone derivative or pharmacologically acceptable salt thereof of the present invention is advantageously selected from the group consisting of the below listed quinone derivatives:

(E)-3-(2-Methoxy-3,5-dimethyl-1,4-benzoquinon-6-yl)-2-[5-(3-pyridyl)pentyl]-2-propenoic acid (E)-3-(2-Methoxy-5,6-dimethyl-1,4-benzoquinon-3-yl)-2-[5-(3-pyridyl)pentyl]-2-propenoic acid (E)-3-(2-Methoxy-5,6-dimethyl-1,4-benzoquinon-3-yl)-2-[6-(3-pyridyl)hexyl]-2-propenoic acid (E)-3-(2,4,5-Trimethoxy-3,6-dimethylphenyl)-2-[5-(3-pyridyl)pentyl]-2-propenoic acid (E)-3-(2,5-Dihydroxy-4-methoxy-3,6-dimethylphenyl)-2-[5-(3-pyridyl)pentyl]-2-propenoic acid (E)-3-(2,3,5-Trimethoxy-4,6-dimethylphenyl)-2-[5-(3-pyridyl)pentyl]-2-propenoic acid.

The quinone derivative portion of the quinone derivative or pharmacologically acceptable salt thereof of the present invention is still advantageously (E)-3-(2-methoxy-3,6-dimethyl-1,4-benzoquinon-5-yl)-2-[5-(3-pyridyl)pentyl]-2-propenoic acid.

The present invention also provides leukotrienes production inhibitor and/or thromboxanes production inhibitor comprising a quinone derivative or pharmacologically acceptable salt thereof of the present invention as an active ingredient.

The present invention further provides a therapeutic and preventive agent for diseases for which leukotrienes production inhibitor and/or thromboxanes inhibitor are efficacious, which comprise a quinone derivative or pharmacologically acceptable salt thereof of the present invention as an active ingredient.

The present invention provides a pharmacological composition which comprises a therapeutically effective amount of the quinone derivative or a pharmacologically acceptable salt thereof of the present invention and a pharmacologically acceptable vehicle.

The present invention also provides use of a quinone derivative or a pharmacologically acceptable salt thereof of the present invention for the making of a medicament for treating a disease in which the production of leukotriene is elevated, and/or, a disease in which the production of thromboxane $A_2$ is elevated.

The present invention further provides use of a quinone derivative or a pharmacologically acceptable salt thereof of the present invention for the making of a medicament for treating a disease selected from the group consisting of asthma, chronic hepatitis, acute hepatitis, drug-induced hepatitis, viral hepatitis, alcoholic hepatitis, icterus, cirrhosis, myocardial infarction, angina pectoris, cerebral embolism, cerebral thrombosis, renal insufficiency, nephrosis and nephritis.

The present invention provides a method for treating a disease which comprises administering a pharmaceutically effective amount of the quinone derivative or pharmacologically acceptable salt thereof of the present invention to a patient suffering from a disease in which the production of leukotriene is elevated, and/or, a patient suffering from a disease in which the production of thromboxane $A_2$ is elevated.

The present invention also provides a method for treating a disease which comprises administering a pharmaceutically effective amount of the quinone derivative or pharmacologically acceptable salt thereof of the present invention to a patient suffering from a disease selected from the group consisting of asthma, chronic hepatitis, acute hepatitis, drug-induced hepatitis, viral hepatitis, alcoholic hepatitis, icterus, cirrhosis, myocardial infarction, angina pectoris, cerebral embolism, cerebral thrombosis, renal insufficiency, nephrosis and nephritis.

DETAILED DESCRIPTION OF THE INVENTION

The compound of the present invention is a quinone derivative represented by the following general formula (I) or a pharmacologically acceptable salt thereof:

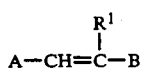

wherein A stands for a group represented by the formula:

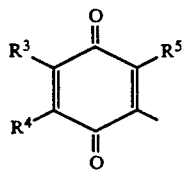

(wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group) or a group represented by the formula:

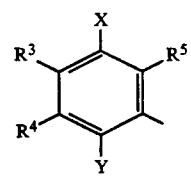

(wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that a case wherein $R^3$ and $R^4$ are each a lower alkoxy group simultaneously is excepted; X and Y are the same or different from each other and each stand for a hydroxyl group or a protected hydroxyl group);

$R^1$ stands for a heteroarylalkyl group; and

B stands for a carboyxl group or a protected carboxyl group.

In the above definition of the compound (I) according to the present invention, the lower alkyl group defined with respect to $R^3$, $R^4$ and $R^5$ is a straight-chain or branched alkyl group having 1 to 8 carbon atoms and examples thereof include methyl group, ethyl group, n-propyl group, isopropyl group, n-butyl group, isobutyl group, sec-butyl group, tert-butyl group, n-pentyl(amyl) group, isopentyl group, neopentyl group, tert-pentyl group, 1-methylbutyl group, 2-methylbutyl group, 3-methylbutyl, 1,2-dimethylpropyl group, n-hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group and octyl group. Among these groups, methyl group, ethyl group, n-propyl group and isopropyl group are desirable.

The lower alkoxy group defined with respect to $R^3$, $R^4$ and $R^5$ is one derived from the above-mentioned lower alkyl group and examples thereof include methoxy group, ethoxy group and n-propoxy group, among which a methoxy group is most desirable.

The alkoxy group constituting the alkoxyalkyl group defined with respect to $R^3$, $R^4$ and $R^5$ has 1 to 8 carbon atoms, preferably 1 to 2 carbon atoms, while the alkyl group, i.e., the alkylene chain constituting it has 1 to 10 carbon atoms.

The alkoxyalkoxy group defined with respect to $R^3$ $R^4$ and $R^5$ is one derived from the above-mentioned lower alkoxy group and examples thereof include methoxymethoxy group, methoxyethoxy group, ethoxyethoxy group and methoxypropoxy group.

The cycloalkyl group constituting the cycloalkylalkoxy group defined with respect to $R^3$, $R^4$ and $R^5$ has 3 to 7 carbon atoms, preferably 5 or 6 carbon atoms, while the alkoxy group constituting it is as defined above with respect to the lower alkoxy group.

The alkyl group constituting the thioalkyl group defined with respect to $R^3$, $R^4$ and $R^5$ has 1 to 8 carbon atoms, preferably 1 or 2 carbon atoms.

In the present invention, both $R^3$ and $R^4$ cannot be each a lower alkoxy group such as a methoxy group simultaneously.

The most desirable combination of $R^3$, $R^4$ and $R^5$ is a case wherein one of $R^3$, $R^4$ and $R^5$ is a lower alkoxy group such as a methoxy group and the others are each a lower alkyl group such as a methyl group and ethyl group, which may be the same or different from each other.

The heteroaryl group constituting the heteroarylalkyl group defined with respect to $R^1$ is preferably a 5- or 6-membered nitrogenous heteroaryl group and particular examples thereof include pyridyl group and imidazolyl group, which may be either unsubstituted or each substituted with a lower alkyl group such as a methyl group and ethyl group, a lower alkoxy group such as a methoxy grooup and ethoxy group or a halogen atom such as chlorine atom and bromine atom.

The alkyl group constituting the heteroarylalkyl group, i.e. the alkylene chain has 1 to 10 carbon atoms, preferably 2 to 8 carbon atoms, still preferably 4 to 6 carbon atoms. Further, the alkylene chain may have a substituted lower alkyl group such as a methyl group and ethyl group at any carbon atom.

The protected hydroxyl group defined with respect to X and Y may be, for example, a hydroxyl group protected with the above-mentioned lower alkyl group such as a methyl group and ethyl group, i.e., an alkoxy group, or a hydroxyl group protected with an acyl group such as an acetyl group, propionyl group, butyroyl group, pivaloyl group and nicotinoyl group, i.e., a group having an ester bond. In short, it may be any one which can be deprotected by some means in vivo to regenerate a hydroxyl group.

The protective group constituting the protected carboxyl group defined with respect to B includes lower alkyl groups such as methyl group, ethyl group and t-butyl group; lower alkyl groups substituted with a phenyl group which may be substituted, such as p-methoxybenzyl group, p-nitrobenzyl group, 3,4-dimethoxybenzyl group, diphenylmethyl group, trityl (triphenylmethyl) group and phenethyl group; halogenated lower alkyl groups such as 2,2,2-trichloroethyl group and 2-iodoethyl group; lower alkanoyloxy lower alkyl groups such as pivaloyloxymethyl group, acetoxymethyl group, propionyloxymethyl group, butyryloxymethyl group, valeryloxymethyl group, 1-acetoxyethyl group, 2-acetoxyethyl group, 1-pivaloyloxyethyl group and 2-pivaloyloxyethyl group; higher alkanoyloxy lower alkyl groups such as palmitoyloxyethyl group, heptadecanoyloxymethyl group and 1-palmitoyloxyethyl group; lower alkoxycarbonyloxy lower alkyl groups such as methoxycarbonyloxymethyl group, 1-butoxycarbonyloxyethyl group, 1-t-butoxycarbonyloxyethyl group, 1-ethoxycarbonyloxyethyl group and 1-(isopropoxycarbonyloxy)ethyl group; carboxy lower alkyl groups such as carboxymethyl group and 2-carboxyethyl group; heterocyclic groups such as 3-phthalidyl group; benzoyloxy lower alkyl groups which may be substituted, such as 4-glycyloxybenzoyloxymethyl group and 4-[N-(t-butoxycarbonyl)-glycyloxy]benzoyloxymethyl group; (substituted dioxolene) lower alkyl groups such as (5-methyl-2-oxo-1,3-dioxolen-4-yl)methyl group; cycloalkylsubstituted lower alkanoyloxy lower alkyl groups such as 1-cyclohexylacetyloxyethyl group; and cycloalkyloxycarbonyloxy lower alkyl groups such as 1-cyclohexyloxycarbonyloxyethyl group.

Further, the protected carboxyl group may be an acid amide.

In short, the protected carboxyl group may be any one which can be deprotected by some means in vivo to regenerate a carboxyl group.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the quinone derivative of the present invention can form a metal salt such as sodium salt, potassium salt, calcium salt and magnesium salt. The pharmacologically acceptable salt of the present invention includes these metal salts.

Although the compound of the present invention may be present as geometrical isomers (including cis- and trans-isomers) because it has a double bond in its molecule, it is needless to say that the present invention includes all of the isomers.

Representative processes for the preparation of the compound according to the present invention will now be described.

PREPARATION PROCESS 1

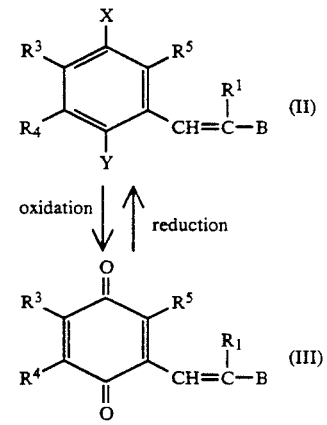

(in the above formulas (II) and (III), X, Y, $R^1$, $R^3$, $R^4$, $R^5$ and B are each as defined above).

In the above reaction scheme, the compounds (II) and (III) are compounds of the present invention. As apparent from the reaction scheme, the benzoquinone derivative represented by the formula (III) can be prepared by reacting the hydroquinone derivative represented by the formula (II) with an oxidizing agent, while the hydroquinone derivative (II) can be prepared by the reduction of the benzoquinone derivative (III).

In the oxidation of the hydroquinone derivative represented by the formula (II), for example, cerium (IV) ammonium nitrate, ferric chloride hexahydrate or lead oxide is used as an oxidizing agent. The amount of the oxidizing agent to be used is preferably 2 to 10 times by mole as much as the hydroquinone. The preferable solvent to be used in the oxidation includes acetonitrile, benzene, ethyl acetate, dioxane, ethanol, 1,2-dimethoxyethane and mixtures thereof with water. The oxidation is conducted at a reaction temperature of 0° to 80° C., preferably 0° to 20° C. The reaction time is generally about 1 to 12 hours.

Contrariwise, in reducing the quinone derivative into the hydroquinone derivative which is one of the objective compounds, sodium borohydride or sodium hydrosulfite is preferably used as a reducing agent. The preferable solvent to be used in the reduction includes ethanol, tetrahydrofuran, ethyl acetate, 1,2-dimethoxyethane and mixtures thereof with water. The reaction temperature is preferably 0° to 40° C., still preferably 0° to 20° C.

PREPARATION PROCESS 2

The hydroquinone derivative (II') which is one of the objective compounds according to the present invention can be prepared also by the following process:

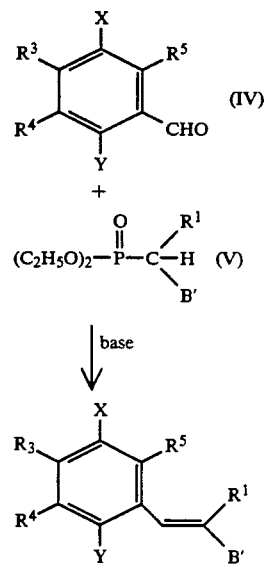

(in the above reaction scheme, $R^1$, $R^3$, $R^4$, $R^5$, X and Y are each as defined above;
and B' is a group selected from among those defined with respect to B except for a carboxyl group).

More precisely, an objective compound represented by the general formula (II') can be prepared by reacting an aldehyde derivative represented by the general formula (IV) with a phosphonate represented by the general formula (V) in the presence of a base through the Wittig reaction [see, e.g., J.A.C.S., 83, 1733(1961)].

The base to be used in this reaction includes alkali metal hydrides such as sodium hydride and potassium hydride; and alkali metal alcoholates such as sodium methylate, sodium ethylate and potassium tert-butoxide. Preferred examples of the solvent to be used therein include benzene, toluene, dichloromethane, tetrahydrofuran, dioxane, dimethoxyethane and dimethylformamide. The reaction temperature is 0° to 100° C., preferably 20° to 80° C.

PREPARATION PROCESS 3

A hydroquinone derivative represented by the general formula (I) wherein B is a carboxyl group can be prepared by the following process:

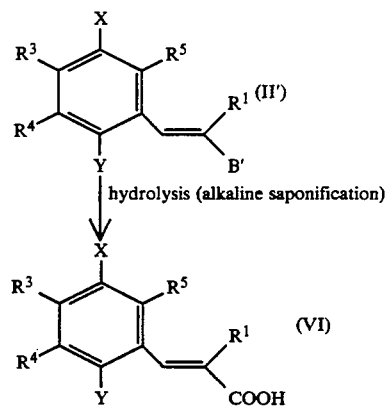

(in the above reaction scheme, $R^1$, $R^3$, $R^4$, $R^5$, X, Y and B' are each as defined above).

More particularly, a compound represented by the general formula (VI) which is one of the objective compounds can be prepared by saponifying a compound represented by the general formula (II') with an alkali according to the conventional process.

This saponification is conducted by the use of the conventional alkali such as alcoholic caustic soda or potash.

The compound (VI) prepared by this process can be easily oxidized into a compound represented by the general formula (VII) which is one of the objective compounds according to the present invention in a similar manner to that described in the Preparation process 1.

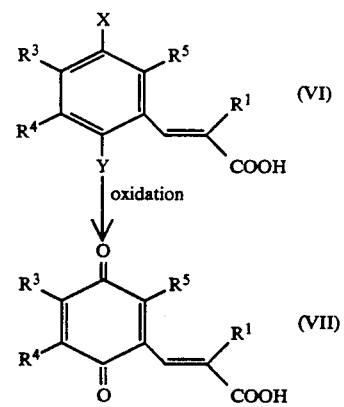

(in the above reaction scheme, $R^1$, $R^3$, $R^4$, $R^5$, X and Y are each as defined above).

PREPARATION PROCESS 4

A compound represented by the general formula (I) wherein B is a protected carboxyl group can be prepared by the following process:

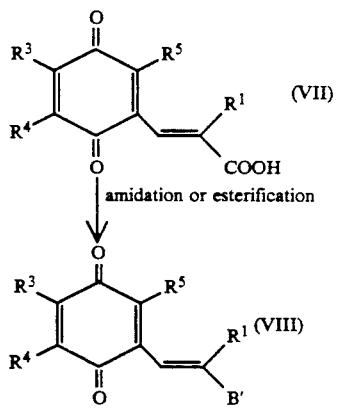

(in the above reaction scheme, $R^1$, $R^3$, $R^4$, $R^5$ and $B'$ are each as defined above).

When the objective compound (II') or (VIII) is an ester, it can be prepared by esterifying a carboxylic acid represented by the general formula (VII) by the conventional process.

The solvent to be used in this esterification may be any one which is inert to the esterification. The reaction temperature is not particularly limited, but varies depending upon the kind of the reactive derivative.

When the objective compound (II') or (VIII) is an amide, it can be prepared by converting a carboxylic acid represented by the general formula (VII) or a reactive derivative thereof into a corresponding amide by the conventional process.

The reactive derivative of the compound (VII) includes acid halides such as acid chloride and acid bromide; acid azide; active esters thereof with N-hydroxybenzotriazole or N-hydroxysuccinimide; symmetric anhydride; and mixed acid anhydride thereof with alkylcarbonic acid or p-toluenesulfonic acid.

When the compound (VII) is a free carboxylic acid, it is preferable to conduct the amidation of the compound (VII) in the presence of a condensing agent such as dicyclohexylcarbodiimide and 1,1'-carbonyldiimidazole.

The amidation is conducted in an organic solvent inert to the amidation, for example, pyridine, tetrahydrofuran, dioxane, ether, benzene, toluene, xylene, methylene chloride, dichloroethane, chloroform, dimethylformamide, ethyl acetate or acetonitrile.

The reaction temperature is not particularly limited but varies depending upon the kind of the reactive derivative.

The processes for the preparation of the compounds according to the present invention can be illustrated by the following reaction scheme:

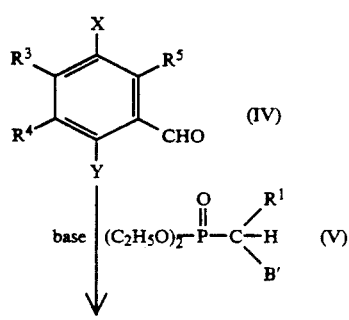

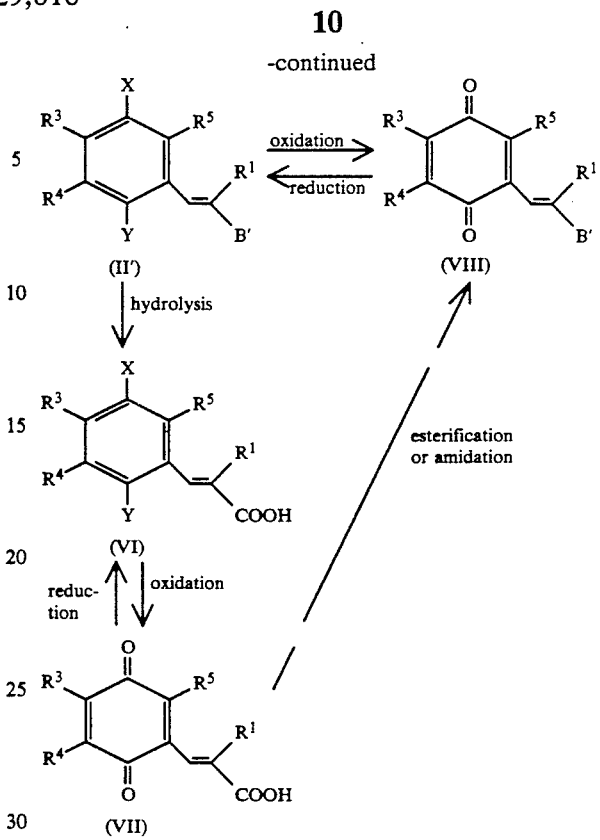

Experimental Examples will now be described in order to illustrate the effect of the compounds according to the present invention.

EXPERIMENTAL EXAMPLE

Inhibitory activity against the production of leukotriene $B_4$ ($LTB_4$) and thromboxane $B_2$ ($TxB_2$) from rat abdominal infiltration cell

METHOD OF EXPERIMENT 10 ml of a 6% (w/v) solution of glycogen (Type II from Oyster, Sigma) in physiological saline was injected into the abdominal cavity of a Fisher male rat having a weight of 150 to 200 g. After 20 to 24 hours, the abdominal exudation cells were recovered therefrom, washed and suspended in the Hanks' balanced salt solution (HBSS) in a concentration of $5 \times 10^6$/ml. This suspension was poured onto a 96-well culture plate (Costar: registered trademark) in which a test drug diluted to a predetermined concentration had been put in an amount of 10 μl/well, in an amount of 100 μl/well. The resulting plate was incubated at 37° C. for 5 minutes. Calcium ionophore A-23187 [Calbiochem (registered trademark)] was added in a final concentration of 2 μg/ml. After the reaction at 37° C. for additional 10 minutes, the plate was put on ice and a BW755C solution was added in a final concentration of 100 μM. The resulting plate was centrifuged at 15000 rpm for 10 minutes. The supernatant was recovered and the amounts of $LTB_4$ and $TxB_2$ in the supernatant were determined by enzyme immunoassay with an EIA kit mfd. by Cayman.

Results

The inhibitory activities ($IC_{50}$) of each compound (shown by the number of Example which will be described below) against the production of leukotriene $B_4$ and thromboxane $B_2$ are given in Table 1.

TABLE 1

| Compound No. | IC$_{50}$ of rat abdominal glycogenic infiltration cell (μM) | |
|---|---|---|
| | LTB$_4$ | TxB$_2$ |
| Ex. 9 | 3.16 | 0.16 |
| Ex. 3 | 1.16 | 0.05 |
| Ex. 6 | 0.59 | 0.12 |
| Ex. 4 | 7.86 | 0.46 |
| Ex. 5 | 3.16 | 0.48 |
| Ex. 7 | 1.39 | 0.09 |
| Ex. 10 | 0.32 | 0.42 |

(Thromboxane A$_2$ is very unstable to treat and naturally turns to thromboxane B$_2$ in 10-20 seconds in the human body. Therefore, thromboxane B$_2$ was used in the tests above).

It can be understood from the results of the above Experimental Examples that the compound of the present invention has an inhibitory activity against the production of both leukotrienes (LTs) and thromboxane (Tx).

Accordingly, the quinone derivatives according to the present invention are efficacious for diseases for which a leukotriene production-inhibiting activity and/or a thromboxane A$_2$ production-inhibiting activity is efficacious. Examples of such diseases include asthma, various liver troubles (such as chronic hepatitis, acute hepatitis, drug-induced hepatitis, viral hepatitis, alcoholic hepatitis, icterus and cirrhosis), ischemic heart diseases (such as myocardial infarction and angina pectoris), cerebral ischemic diseases (such as cerebral embolism and cerebral thrombosis) and various kidney diseases (such as renal insufficiency, nephrosis and nephritis).

Further, the compounds of the present invention are highly safe and therefore are valuable in this respect.

In using the compounds of the present invention as an inhibitor against leucotriene and/or thromboxane production to treat or prevent various diseases, they may be each administered orally as a powder, granule, capsule or syrup, or parenterally as a suppository, injections, external preparation or drop. Although the dose of the compound remarkably varies depending upon the symptom, the age of a patient and the kind of disease, it is generally about 0.1 to 2,000 mg, preferably about 2 to 500 mg, still preferably about 5 to 150 mg per adult a day, which may be administered in one to several portions a day.

The compounds of the present invention can be converted into pharmaceutical preparations by the use of the conventional excipients carriers according to the conventional processes.

A solid preparation for oral administration according to the present invention is prepared by adding a vehicle and, if necessary, a binder, disintegrator, lubricant, colorant and/or corrigent to an active ingredient and shaping the obtained mixture into a tablet, coated tablet, granule, powder or capsule.

Examples of the vehicle include lactose, corn starch, sucrose, glucose, sorbitol, crystalline cellulose and silicon dioxide; those of the binder include polyvinyl alcohol, polyvinyl ether, ethylcellulose, methylcellulose, gum arabic, tragacanth, gelatin, shellac, hydroxypropylcellulose, hydroxylpropylmethylcellulose, calcium citrate, dextrin and pectin; those of the lubricant include magnesium stearate, talc, polyethylene glycol, silica and hardened vegetable oil; those of the colorant include those authorized as pharmaceutical additives; and those of the corrigent include cocoa powder, menthae herba (menthol), aromatic powder, mentha oil (peppermint oil), borneol and powdered cinnamon bark. Of course, the tablet and granule may be suitably coated with sugar, gelatin and the like, if necessary.

An injection according to the present invention is prepared by adding a pH modifier, buffer, stabilizer and/or solubilizing agent to an active ingredient at need and converting the mixture into an injection for subcutaneous, intramuscular or intravenous administration.

EXAMPLE

Examples of the present invention will now be described below, though it is needless to say that the present invention is not limited to them.

The preparation of the starting compounds for preparing the compounds of the present invention will be described in the following Preparative Examples.

The symbols in the chemical formulas which will be given below have the following meaning respectively:

Me: methyl group, Et: ethyl group,
n-Bu: n-butyl group, n-Hep: n-heptyl group,
MOMO: methoxymethoxy group

PREPARATIVE EXAMPLE 1

Ethyl 2-diethylphosphono-7-(3-pyridyl)heptanoate

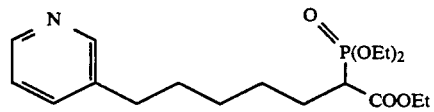

221 g of 5-(3-pyridyl)pentanol was dissolved in methylene chloride (2 l), followed by the addition of 142 g of triethylamine. Mesyl chloride (161 g) was dropped into the obtained mixture under cooling with ice. After the completion of the dropping, the obtained mixture was stirred for one hour under cooling with ice. The organic layer was washed with water twice, dried over magnesium sulfate and distilled in a vacuum to remove the solvent. A pale-red oil was obtained as a residue.

Separately, sodium hydride (55% oil suspension, 59 g) was suspended in N,N-dimethylformamide (500 ml), followed by the dropwise addition of 300 g of triethyl phosphonoacetate. The obtained mixture was stirred at 50° to 60° C. for one hour, followed by the addition of a solution of the above residue (a pale-red oil) in N,N-dimethylformamide (500 ml). The obtained mixture was stirred at 50° to 60° C. for 18 hours. After the completion of the reaction, ethyl acetate (3 l) was added to the reaction mixture and the mixture was washed with a saturated aqueous solution of sodium chloride twice. The organic layer was dried over anhydrous magnesium sulfate and distilled in a vacuum to remove the solvent. The residue was purified by silica gel column chromatography [n-hexane/ethyl acetate (30%-50%), ethyl acetate-methanol (5%)] to give 226 g of the title compound as a pale-red oil.

EXAMPLE 1

Ethyl (E)-3-(2,4,5-trimethoxy-3,6-dimethylphenyl)-2-[5-(3-pyridyl)pentyl]-2-propenoate

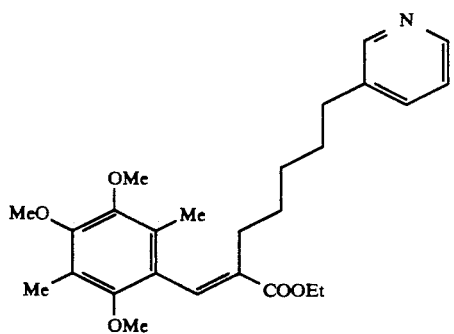

24 g (0.6 mol) of 60% sodium hydride was suspended in 200 ml of N,N-dimethylformamide and the obtained suspension was stirred at room temperature.

A solution of 222 g (0.6 mol) of the ethyl 2-diethylphosphono-7-(3-pyridyl)heptanoate (a Wittig reagent) prepared in the Preparative Example 1 in 300 ml of N,N-dimethylformamide was gradually dropped into the above suspension. After the completion of the dropping, the obtained mixture was stirred at room temperature for one hour to give a transparent solution. A solution of 122 g (0.54 mol) of 2,4,5-trimethoxy-3,6-dimethylbenzaldehyde in 200 ml of N,N-dimethylformamide was dropped into the transparent solution. The obtained mixture was stirred overnight under heating at 50° C.

The reaction mixture was poured onto 1 l of ice-water. The obtained mixture was extracted with 1 l of ethyl acetate twice. The organic layer was dried over magnesium sulfate and distilled to remove the solvent. The residue was subjected to silica gel column chromatography [solvent: n-hexane→ethyl acetate (10%→30%)/n-hexane].

177 g of the title compound was obtained as a pale-yellow oil.

$^1$H-NMR (400 MHz, CDCl$_3$) δ (ppm); 1.21 (tt, J=7.5, 7.5 Hz, 2H), 1.35 (t, J=7.1 Hz, 3H), 1.38 (tt, J=7.5, 7.5 Hz, 2H), 1.46 (tt, J=7.5, 7.5 Hz, 2H), 2.07 (s, 3H), 2.16 (t, J=7.5 Hz, 2H), 2.16 (s, 3H), 2.48 (t, J=7.5 Hz, 2H), 3.54 (s, 3H), 3.76 (s, 3H), 3.82 (s, 3H), 4.12 (q, J=7.1 Hz, 2H), 7.16 (dd, J=5.5, 7.8 Hz, 1H), 7.39 (dt, J=1.5, 5.5 Hz, 1H), 7.45 (s, 1H), 8.36 (d, J=1.5 Hz, 1H), 8.39 (dd, J=1.5, 5.5 Hz, 1H).

EXAMPLE 2

(E)-3-(2,4,5-Trimethoxy-3,6-dimethylphenyl)-2-[5-(3-pyridyl)pentyl]-2-propenoic acid

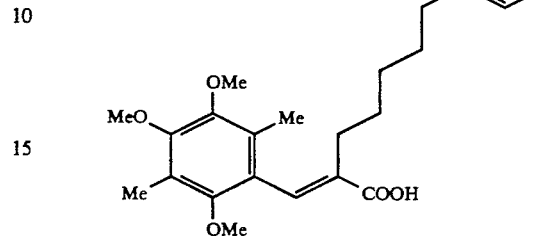

177 g (0.39 mol) of the ester prepared in Example 1 was dissolved in 500 ml of ethanol, followed by the addition of 100 ml of an aqueous solution of 78 g of sodium hydroxide. The obtained mixture was heated under reflux for one hour, followed by the addition of 1 l of ice. The obtained mixture was neutralized with 6N hydrochloric acid. The resulting mixture was extracted with 1 l of ethyl acetate twice. The organic layer was washed with an aqueous solution of sodium chloride, dried over magnesium sulfate and distilled to remove the solvent. 159 g of the title compound was obtained as a colorless oil.

$^1$H-NMR (400 MHz, CDCl$_3$) δ (ppm); 1.24 (tt, J=7.6, 7.6 Hz, 2H), 1.47 (tt, J=7.6, 7.6 Hz, 2H), 1.52 (tt, J=7.6, 7.6 Hz, 2H), 2.09 (s, 3H), 2.17 (s, 3H), 2.20 (t, J=7.6 Hz, 2H), 2.54 (t, J=7.6 Hz, 2H), 3.57 (s, 3H), 3.78 (s, 3H), 3.83 (s, 3H), 7.23 (dd, J=5.0, 7.6 Hz, 1H), 7.48 (bd, J=7.6 Hz, 1H), 7.59 (s, 1H), 8.46 (bs, 2H).

EXAMPLE 3

(1) (E)-3-(2-Methoxy-3,6-dimethyl-1,4-benzoquinon-5-yl)-2-[5-(3-pyridyl)pentyl]-2-propenoic acid

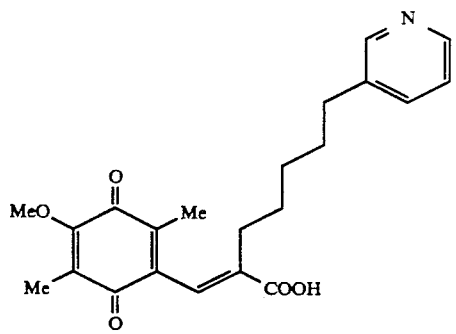

159 g (0.39 mol) of the carboxylic acid prepared in the Example 2 was dissolved in an acetonitrile (800 ml)/water (400 ml) mixture. The obtained solution was cooled in an ice bath, followed by the gradual dropwise addition of 700 ml of an aqueous solution of 527 g (0.96 mol) of cerium (IV) ammonium nitrate. The obtained mixture was stirred for 30 minutes and the pH thereof was adjusted to 5 with a saturated solution of sodium hydrogencarbonate, followed by the addition of 3 l of water. The obtained mixture was extracted with 6 l of ethyl acetate twice. The organic layer was washed with a saturated aqueous solution of sodium chloride, dried over magnesium sulfate and distilled to remove the solvent. The obtained oil was crystallized from a small amount of ethyl acetate to give 114 g of a yellow crystal. This crystal was recrystallized from an ethanol/water mixture to give 90 g of the title compound.

m.p.: 134° to 135° C.

$^1$H-NMR (400 MHz, CDCl$_3$) δ (ppm); 1.26 (tt, J=7.0, 7.0 Hz, 2H), 1.50 (tt, J=7.0, 7.0 Hz, 2H), 1.61 (tt, J=7.0, 7.0 Hz, 2H), 1.95 (s, 3H), 1.96 (s, 3H), 2.12 (t, J=7.0 Hz, 2H), 2.60 (t, J=7.0 Hz, 2H), 4.01 (s, 3H), 7.26 (s, 1H), 7.27 (dd, J=5.0, 8.5 Hz, 1H), 7.55 (bd, J=8.5 Hz, 1H), 8.44 (bd, J=5.0 Hz, 1H), 8.50 (bs, 1H).

(2) (E)-3-(2-Methoxy-3,6-dimethyl-1,4-benzoquinon-5-yl)-2-[5-(3-pyridyl)pentyl]-2-propenoic acid hydrochloride

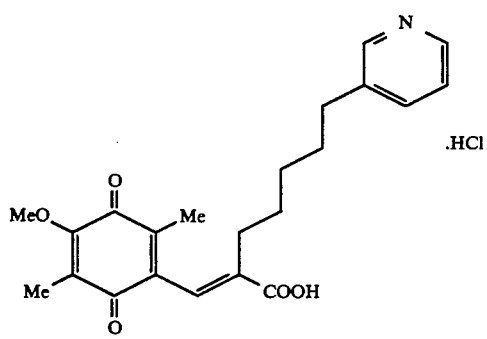

A hydrochloride of the compound described above (1) was prepared by the conventional process.

m.p.: 138° to 139° C.

$^1$H-NMR (400 MHz, DMSO-d$_6$) δ (ppm); 1.18 (tt, J=7.2, 7.2 Hz, 2H), 1.37 (tt, J=7.2, 7.2 Hz 2H), 1.54 (tt, J=7.2, 7.2 Hz, 2H), 1.82 (s, 3H), 1.84 (s, 2H), 2.04 (t, J=7.2 Hz, 2H), 2.71 (t, J=7.2 Hz, 2H), 3.92 (s, 3H), 7.04 (d, J=1.2 Hz, 1H), 7.97 (dd, J=2.4, 8.0 Hz, 1H), 8.41 (d, J=8.0 Hz, 1H), 8.76 (d, J=5.6 Hz, 1H), 8.79 (s, 1H).

EXAMPLE 4

(E)-3-(2,5-Dihydroxy-4-methoxy-3,6-dimethylphenyl)-2-[5-(3-pyridyl)pentyl]-2-propenoic acid

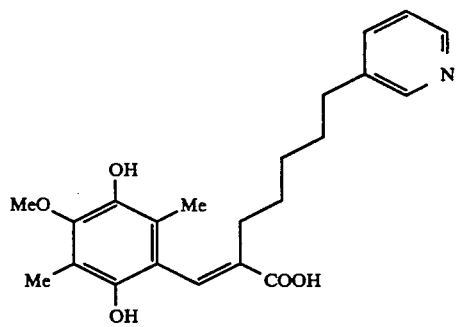

1.0 g of the quinone prepared in the Example 3 (1) was suspended in 150 ml of ethyl acetate and the obtained suspension was fully mixed with a solution of 2 g of sodium hydrosulfite in 50 ml of water. The organic layer was separated, dried over anhydrous magnesium sulfate and concentrated in a vacuum to give 660 mg of the title compound as a white amorphous substance.

$^1$H-NMR (400 MHz, CDCl$_3$) δ (ppm); 1.21 (tt, J=7.0, 7.0 Hz, 2H), 1.44 (tt, J=7.0, 7.0 Hz, 2H), 1.51 (tt, J=7.0, 7.0 Hz, 2H), 2.06 (s, 3H), 2.17 (s, 3H), 2.23 (t, J=7.0 Hz, 2H), 2.54 (t, J=7.0 Hz, 2H), 3.76 (s, 3H), 5.22 (bs, 2H), 7.26 (dd, J=5.5, 7.0 Hz, 1H), 7.43 (s, 1H), 7.51 (dd, J=1.5, 7.0 Hz, 1H), 8.40–8.47 (m, 2H).

EXAMPLES 5 TO 22

The compounds listed in the following Tables 2 to 7 were each prepared in a similar manner to that of the Example 1.

TABLE 2

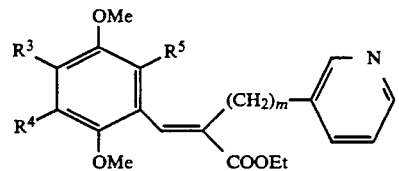

| Ex. No. | R$^3$ | R$^4$ | R$^5$ | n | Properties | $^1$H-NMR spectrum TMS as internal reference, δ value (ppm) |
|---|---|---|---|---|---|---|
| 5 | n-HepO | Me | Me | 5 | colorless oil | 0.90 (t, J=7.0Hz, 3H), 1.16–1.58 (m, 14H), 1.26 (t, J=7.0Hz, 3H), 1.76 (tt, J=7.0, 7.0Hz, 2H), 2.07 (s, 3H), 2.08–2.20 (m, 2H), 2.17 (s, 3H), 2.48 (t, J=7.0Hz, 2H), 3.54 (s, 3H), 3.75 (s, 3H), 3.91 (t, J=7.0Hz, 2H), 4.27 (q, J=7.0Hz, 2H), 7.18 (dd, J=5.0, 8.0Hz, 1H), 7.40 (bd, J=8.0Hz, 1H), 7.46 (s, 1H), 8.38 (d, J=1.5Hz, 1H), 8.40 (bd, J=5.0Hz, 1H) |
| 6 | Me | MeO | Me | 5 | colorless oil | 1.21 (tt, J=8.0, 8.0Hz, 2H), 1.35 (t, J=7.2Hz, 3H), 1.40 (t, J=8.0Hz, 2H), 1.48 (tt, J=8.0, 8.0Hz, 2H), 2.07 (s, 3H), 2.15 (t, J=8.0Hz, 2H), 2.21 (s, 3H), 2.49 (t, J=8.0Hz, 2H), 3.65 (s, 3H), 3.70 (s, 3H), 3.77 (s, 3H), 4.28 (q, J=7.2Hz, 2H), 7.16 (dd, J=4.8, 7.6Hz, 1H), 7.39 (d, J=8.0Hz, 1H), 7.44 (s, 1H), 8.36 (d, J=1.6Hz, 1H), 8.40 (dd, J=1.6, 4.8Hz, 1H) |
| 7 | Me | n-BuO | Me | 5 | colorless oil | 0.97 (t, J=8.0Hz, 3H), 1.22 (tt, J=7.6Hz, 2H), 1.36 (t, J=8.0Hz, 3H), 1.38–1.52 (m, 6H), 1.725 (tt, J=7.6, 7.6Hz, 2H), 2.06 (s, 3H), 2.15 (t, J=7.6Hz, 2H), 2.20 (s, 3H), 2.48 (t, J=7.6, 7.6Hz, 2H), 3.65 (s, 3H), 3.67 (s, 3H), 3.88 (t, J=8.0Hz, 2H), 4.275 (q, J=8.0Hz, 2H), 7.17 (dd, J=4.8, 7.6Hz, 1H), 7.39 (d, J=7.6Hz, 1H), 7.45 (s, 1H), 8.36 (s, 1H), 8.41 (d, J=4.8Hz, 1H) |

TABLE 3

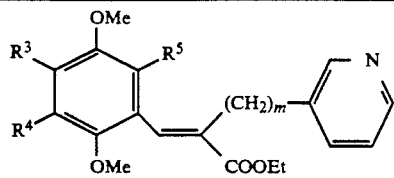

| Ex. No. | R³ | R⁴ | R⁵ | n | Properties | ¹H-NMR spectrum TMS as internal reference, δ value (ppm) |
|---|---|---|---|---|---|---|
| 8 | Me | n-BuO | Me | 3 | colorless oil | 0.98 (t, J=8.0Hz, 3H), 1.34 (t, J=8.0Hz, 3H), 1.51 (q, J=7.6Hz, 2H), 1.67-1.80 (m, 4H), 2.06 (s, 3H), 2.20 (t, J=7.6Hz, 2H), 2.23 (s, 3H), 2.47 (t, J=7.6Hz, 2H), 3.67 (s, 6H), 3.89 (t, J=8.0H, 2H), 4.27 (q, J=8.0Hz, 2H), 7.09 (dd, J=4.8, 7.6Hz, 1H), 7.32 (d, J=7.6Hz, 1H), 7.48 (s, 1H), 8.31 (s, 1H), 8.37 (d, J=4.8Hz, 1H) |
| 9 | Me | n-HepO | Me | 5 | colorless oil | 0.89 (t, J=7.0Hz, 3H), 1.21 (tt, J=8.0, 8.0Hz, 2H), 1.25-1.52 (m, 12H), 1.35 (t, J=7.5Hz, 3H), 1.74 (tt, J=8.0, 8.0Hz, 2H), 2.07 (s, 3H), 2.15 (t, J=8.0Hz, 2H), 2.21 (s, 3H), 2.48 (t, J=8.0Hz, 2H), 3.66 (s, 3H), 3.68 (s, 3H), 3.88 (t, J=6.5Hz, 2H), 4.27 (q, J=7.5Hz, 2H), 7.16 (dd, J=4.8, 7.5Hz, 1H), 7.39 (d, J=7.5Hz, 1H), 7.45 (s, 1H), 8.36 (d, J=1.2Hz, 1H), 8.41 (dd, J=1.2, 4.8Hz, 1H) |
| 10 | MeO | Me | Me | 3 | colorless oil | 1.34 (t, J=7.1Hz, 3H), 1.70 (tt, J=7.6, 7.6Hz, 2H), 2.06 (s, 3H), 2.16 (s, 3H), 2.20 (t, J=7.6Hz, 2H), 2.48 (t, J=7.6Hz, 2H), 3.54 (s, 3H), 3.78 (s, 3H), 3.86 (s, 3H), 4.27 (q, J=7.1Hz, 2H), 7.11 (dd, J=4.8, 8.0Hz, 1H), 7.33 (d, J=8.0Hz, 1H), 7.49 (s, 1H), 8.32 (d, J=2.0Hz, 1H), 8.37 (dd, J=2.0, 4.8Hz, 1H) |

TABLE 4

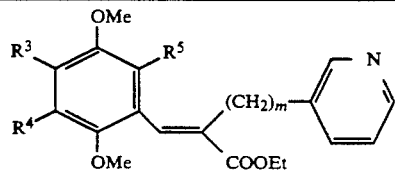

| Ex. No. | R³ | R⁴ | R⁵ | n | Properties | ¹H-NMR spectrum TMS as internal reference, δ value (ppm) |
|---|---|---|---|---|---|---|
| 11 | Me | Me | MeO | 5 | colorless oil | 1.30 (tt, J=7.6, 7.6Hz, 2H), 1.42-1.57 (m, 4H), 2.15 (s, 3H), 2.19 (s, 3H), 2.28 (t, J=7.6Hz, 2H), 2.64 (t, J=7.6Hz, 2H), 3.56 (s, 3H), 3.72 (s, 3H), 3.76 (s, 3H), 7.24 (m, 1H), 7.49 (d, J=7.2Hz, 1H), 7.64 (s, 1H), 8.43 (bs, 2H) |
| 12 | MeO | Me | Me | 4 | colorless oil | 1.33 (t, J=7.2Hz, 3H), 1.41 (tt, J=7.2, 7.2Hz, 2H), 1.49 (tt, J=7.2, 7.2Hz, 2H), 2.06 (s, 3H), 2.17 (s, 3H), 2.21 (t, J=7.2Hz, 2H), 2.47 (t, J=7.2Hz, 2H), 3.52 (s, 3H), 3.77 (s, 3H), 3.84 (s, 3H), 4.27 (q, J=7.2Hz, 2H), 7.15 (dd, J=4.8, 8.0Hz, 1H), 7.37 (d, J=8.0Hz, 1H), 7.47 (s, 1H), 8.35 (d, J=1.6Hz, 1H), 8.39 (dd, J=1.6, 4.8Hz, 1H) |
| 13 | MeO | Me | Me | 6 | colorless oil | 1.19 (t, J=3.2Hz, 4H), 1.35 (t, J=7.0Hz, 5H), 1.51 (t, J=8.0Hz, 2H), 2.08 (s, 3H), 2.16 (t, J=8.0Hz, 2H), 2.17 (s, 3H), 2.52 (t, J=8.0Hz, 2H), 3.55 (s, 3H), 3.78 (s, 3H), 3.85 (s, 3H), 4.27 (q, J=7.0Hz, 2H), 7.19 (dd, J=4.8, 7.6Hz, 1H), 7.44 (d, J=7.6Hz, 1H), 7.46 (s, 1H), 8.40 (s, 1H), 8.42 (d, J=4.8Hz, 1H) |

TABLE 5

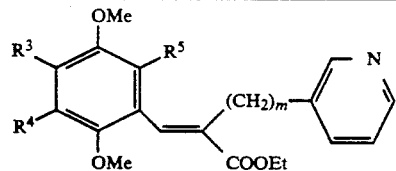

| Ex. No. | R³ | R⁴ | R⁵ | n | Properties | ¹H-NMR spectrum TMS as internal reference, δ value (ppm) |
|---|---|---|---|---|---|---|
| 14 | Me | MeO | Me | 6 | colorless oil | 1.71-1.23 (m, 4H), 1.33 (t, J=8.0Hz, 5H), 1.51 (tt, J=8.0, 8.0Hz, 2H), 2.07 (s, 3H), 2.12 (t, J=8.0Hz, 2H), 2.21 (s, 3H), 2.51 (t, J=8.0Hz, 2H), 3.66 (s, 3H), 3.69 (s, 3H), 3.80 (s, 3H), 4.27 (q, J=8.0Hz, 2H), 7.18 (dd, J=4.8, 7.6Hz, 1H), 7.43 (d, J=7.6Hz, 1H), 7.46 (s, 1H), 8.38 (s, 1H), 8.41 (d, J=4.8Hz, 1H) |
| 15 | Me | Me | MeO | 6 | colorless oil | 1.21-1.25 (m, 4H), 1.34 (t, J=8.0Hz, 3H), 1.41 (tt, J=8.0, 8.0Hz, 2H), 1.55 (tt, J=8.0, 8.0Hz, 2H), 2.15 (s, 3H), 2.20 (s, 3H), 2.27 (t, J=8.0Hz, 2H), 2.53 (t, J=8.0Hz, 2H), 3.57 (s, 3H), 3.72 (s, 3H), 3.77 (s, 3H), 4.28 (q, J=8.0Hz, 2H), 7.20 (dd, J=4.8, 7.6Hz, 1H), 7.46 (d, J=7.6Hz, 1H), 7.51 (s, 1H), 8.40 (s, 1H), 8.43 (d, J=4.8Hz, 1H) |
| 16 | H | Me | MeO | 5 | colorless oil | 1.25 (t, J=8.0Hz, 2H), 1.35 (t, J=9.0Hz, 3H), 1.40-1.53 (m, 4H), 2.24 (s, 3H), 2.27 (t, J=8.0Hz, 2H), 2.50 (t, J=8.0Hz, 2H), 3.56 (s, 3H), 3.68 (s, 3H), 3.83 (s, 3H), 4.28 (q, J=9.0Hz, 2H), 6.70 (s, 1H), 7.16 (dd, J=5.0, 9.0Hz, 1H), 7.42 (bd, J=9.0Hz, 1H), 7.51 (s, 1H), 8.36 (bs, 1H), 8.40 (bd, J=5.0Hz, 1H) |

TABLE 6

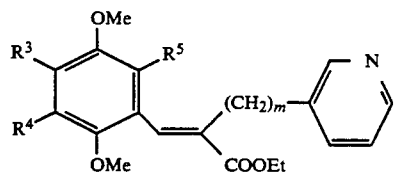

| Ex. No. | R³ | R⁴ | R⁵ | n | Properties | ¹H-NMR spectrum TMS as internal reference, δ value (ppm) |
|---|---|---|---|---|---|---|
| 17 | Me | Me | Me | 5 | colorless oil | 1.17–1.52 (m, 6H), 1.33 (t, J=7.2Hz, 3H), 2.00 (s, 3H), 2.15 (s, 3H), 2.19 (s, 3H), 2.12–2.22 (m, 2H), 2.46 (t, J=7.0Hz, 2H), 3.53 (s, 3H), 3.63 (s, 3H), 4.26 (q, J=7.2Hz, 2H), 7.16 (dd, J=4.0, 7.6Hz, 1H), 7.38 (dt, J=1.6, 7.6Hz, 1H), 7.50 (s, 1H), 8.35 (d, J=1.6Hz, 1H), 8.40 (dd, J=1.6, 4.0Hz, 1H) |
| 18 | Me |  | Me | 5 | colorless oil | 1.12 (dq, J=4.0, 12.0Hz, 2H), 1.16–1.30 (m, 4H), 1.34 (t, J=8.0Hz, 3H), 1.40 (t, J=8.0, 2H), 1.48 (tt, J=8.0, 8.0Hz, 2H), 1.66–1.80 (m, 5H), 1.88 (bd, J=12.0Hz, 2H), 2.07 (s, 3H), 2.15 (t, J=8.0Hz, 2H), 2.21 (s, 3H), 2.48 (t, J=8.0Hz, 2H), 3.66 (s, 3H), 3.67 (d, J=16Hz, 2H), 3.68 (s, 3H), 4.28 (q, J=8.0Hz, 2H), 7.16 (dd, J=4.8, 7.6Hz, 1H), 7.39 (d, J=7.6Hz, 1H), 7.45 (s, 1H), 8.37 (d, J=1.6Hz, 1H), 8.41 (dd, J=1.6, 4.8Hz, 1H) |
| 19 | EtO | Me | Me | 5 | colorless oil | 1.20 (m, 2H), 1.30–1.40 (m, 10H), 2.06 (s, 3H), 2.14–2.20 (2, 5H), 2.46 (t, J=8.0Hz, 2H), 3.53 (s, 3H), 3.74 (s, 3H), 4.00 (q, J=7.0Hz, 2H), 4.26 (q, J=7.0Hz, 2H), 7.13 (s, 1H), 7.37 (d, J=8.0Hz, 1H), 7.48 (s, 1H), 8.35 (bs, 2H) |

TABLE 7

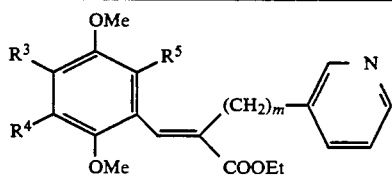

| Ex. No. | R³ | R⁴ | R⁵ | n | Properties | ¹H-NMR spectrum TMS as internal reference, δ value (ppm) |
|---|---|---|---|---|---|---|
| 20 | Me |  | Me | 5 | colorless oil | 1.19 (tt, J=7.5, 7.5Hz, 2H), 1.30–1.35 (m, 5H), 1.45 (tt, J=7.5, 7.5Hz, 2H), 1.73 (t, J=8.0Hz, 2H), 2.08 (s, 3H), 2.15 (t, J=7.5Hz, 2H), 3.33 (s, 3H), 3.40 (t, J=8.0Hz, 2H), 3.55 (s, 3H), 3.63 (s, 3H), 4.27 (q, J=7.5Hz, 2H), 7.16 (dd, J=4.8, 8.0Hz, 1H), 7.37 (d, J=8.0Hz, 1H), 7.50 (s, 1H), 8.35 (s, 1H), 8.40 (d, J=4.8Hz, 1H) |
| 21 | MeS | Me | Me | 5 | pale-yellow oil | 1.22 (tt, J=7.5, 7.5Hz, 2H), 1.32 (t, J=8.0Hz, 3H), 1.39 (tt, J=7.5, 7.5Hz, 2H), 1.47 (tt, J=7.5, 7.5Hz, 2H), 2.11 (s, 3H), 2.14 (t, J=7.5Hz, 2H), 2.38 (s, 3H), 2.42 (s, 3H), 2.49 (t, J=7.5Hz, 2H), 3.55 (s, 3H), 3.78 (s, 3H), 4.27 (q, J=8.0Hz, 2H), 7.17 (dd, J=4.5, 7.5 Hz, 1H), 7.39 (d, J=7.5Hz, 1H), 7.46 (s, 1H), 8.37 (s, 1H), 8.40 (d, J=4.5Hz, 1H) |
| 22 | MOMO | Me | Me | 5 | pale-yellow oil | 1.20 (tt, J=8.0, 8.0Hz, 2H), 1.32 (t, J=8.5Hz, 3H), 1.33 (tt, J=8.0, 8.0 Hz, 2H), 1.48 (tt, J=8.0, 8.0Hz, 2H), 2.05 (s, 3H), 2.16 (t, J=8.0Hz, 2H), 2.22 (s, 3H), 2.49 (t, J=8.0Hz, 2H), 3.53 (s, 3H), 3.60 (s, 3H), 3.72 (s, 3H), 4.26 (t, J=8.5Hz, 2H), 5.08 (s, 2H), 7.16 (dd, J=4.5, 7.5Hz, 1H), 7.40 (bd, J=7.5Hz, 1H), 7.46 (s, 1H), 8.35 (bs, 1H), 8.40 (d, J=4.5Hz, 1H) |

EXAMPLE 23

Ethyl (E)-3-(2-methoxy-3,6-dimethyl-1,4-benzoquinon-5-yl)-2-[6-(3-pyridyl)hexyl]-2-propenoate hydrochloride

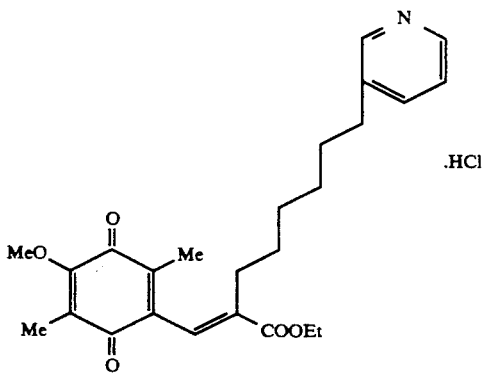

0.60 g of the ethyl (E)-3-(2,4,5-trimethoxy-3,6-dimethylphenyl)-2-[6-(3-pyridyl)hexyl]-2-propenoate prepared in the Example 13 was dissolved in an acetonitrile (20 ml)/water (10 ml) mixture. The obtained solution was stirred under cooling with ice, followed by the addition of 1.66 g of cerium (IV) ammonium nitrate in portions. The obtained mixture was stirred under cooling with ice for 3 hours, followed by the addition of 100 ml of ethyl acetate. The obtained mixture was washed with a saturated aqueous solution of sodium hydrogencarbonate twice and thereafter with a saturated aqueous solution of sodium chloride, dried over magnesium sulfate and filtered. The filtrate was concentrated to 10 ml, adsorbed on a silica gel column and eluted with an ethyl acetate/n-hexane (1:1) mixture. The fractions containing the objective compound were combined and dry hydrogen chloride gas was bubbled thereinto for one minute. The solvent was distilled away in a vacuum. 0.40 g of the title compound was obtained as a yellow oil.

$^1$H-NMR (DMSO-$d_6$) $\delta$ (ppm); 1.07–1.33 (m, 6H), 1.23 (t, J=7.0 Hz, 3H), 1.45–1.57 (t, J=8.0 Hz, 2H), 1.80 (s, 3H), 1.81 (s, 3H), 2.03 (t, J=8.0 Hz, 2H), 2.49 (t, J=8.0 Hz, 2H), 3.91 (s, 3H), 4.18 (q, J=7.0 Hz, 2H), 7.03 (s, 1H), 7.93 (bt, J=8.0 Hz, 1H), 8.37 (bd, J=8.0 Hz, 1H), 8.73 (d, J=8.0 Hz, 1H), 8.76 (s, 1H).

EXAMPLES 24 TO 41

The compounds listed in the following Tables 8 to 13 were each prepared in a similar manner to that of the Example 2:

TABLE 8

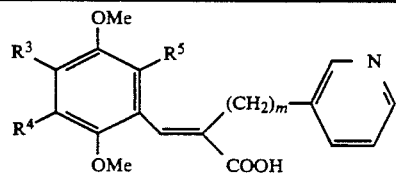

| Ex. No. | $R^3$ | $R^4$ | $R^5$ | n | Properties | $^1$H-NMR spectrum TMS as internal reference, $\delta$ value (ppm) |
|---|---|---|---|---|---|---|
| 24 | MeO | Me | Me | 5 | colorless oil | 1.24 (tt, J=7.6, 7.6Hz, 2H), 1.47 (tt, J=7.6, 7.6Hz, 2H), 1.52 (tt, J=7.6, 7.6Hz, 2H), 2.09 (s, 3H), 2.17 (s, 3H), 2.20 (t, J=7.6Hz, 2H), 2.54 (t, J=7.6Hz, 2H), 3.57 (s, 3H), 3.78 (s, 3H), 3.83 (s, 3H), 7.28 (dd, J=5.0, 7.6Hz, 1H), 7.48 (bd, J=7.6Hz, 1H), 7.59 (s, 1H), 8.46 (bs, 2H) |
| 25 | Me | MeO | Me | 5 | colorless oil | 1.21 (tt, J=8.0, 8.0Hz, 2H), 1.35 (t, J=7.2Hz, 3H), 1.40 (t, J=8.0Hz, 2H), 1.48 (tt, J=8.0, 8.0Hz, 2H), 2.07 (s, 3H), 2.15 (t, J=8.0Hz, 2H), 2.21 (s, 3H), 2.49 (t, J=8.0Hz, 2H), 3.65 (s, 3H), 3.70 (s, 3H), 3.77 (s, 3H), 4.28 (q, J=7.2Hz, 2H), 7.16 (dd, J=4.8, 7.6Hz, 1H), 7.39 (d, J=8.0Hz, 1H), 7.44 (s, 1H), 8.36 (d, J=1.6Hz, 1H), 8.40 (dd, J=1.6, 4.8Hz, 1H) |
| 26 | Me | n-BuO | Me | 5 | colorless oil | 0.96 (t, J=8.0Hz, 3H), 1.13 (bs, 2H), 1.40–1.55 (m, 4H), 1.71 (tt, J=7.6, 7.6Hz, 2H), 2.05 (s, 3H), 2.13 (t, J=7.6Hz, 2H), 2.19 (s, 3H), 2.48 (t, J=7.6Hz, 2H), 3.62 (bs, 6H), 3.86 (t, J=8.0Hz, 2H), 7.17 (d, J=7.6Hz, 1H), 7.40 (d, J=7.6Hz, 1H), 7.51 (s, 1H), 8.44 (s, 2H) |

TABLE 9

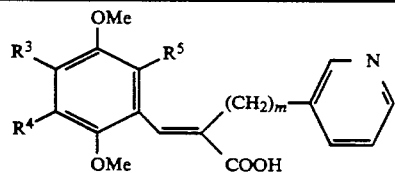

| Ex. No. | $R^3$ | $R^4$ | $R^5$ | n | Properties | $^1$H-NMR spectrum TMS as internal reference, $\delta$ value (ppm) |
|---|---|---|---|---|---|---|
| 27 | Me | n-BuO | Me | 3 | colorless oil | 0.98 (t, J=8.0Hz, 3H), 1.51 (q, J=7.6Hz, 2H), 1.71–1.85 (m, 4H), 2.04 (s, 3H), 2.22 (bs, 5H), 2.52 (t, J=7.6Hz, 2H), 3.66 (s, 6H), 3.90 (t, J=8.0Hz, 2H), 7.16 (bs, 1H), 7.39 (d, J=7.6Hz, 1H), 7.56 (s, 1H), 8.42 (bs, 1H), 8.51 (bs, 1H) |
| 28 | Me | n-HepO | Me | 5 | colorless oil | 0.90 (t, J=8.0Hz, 3H), 1.20–1.38 (m, 10H), 1.41–1.54 (m, 4H), 1.76 (tt, J=7.6, 7.6Hz, 2H), 2.08 (s, 3H), 2.18 (t, J=7.6Hz, 2H), 2.21 (s, 3H), 2.53 (t, J=7.6Hz, 2H), 3.67 (s, 3H), 3.69 (s, 3H), 3.90 (t, J=8.0Hz, 2H), 7.23 (t, J=7.6Hz, 1H), 7.47 (d, J=7.6Hz, 1H), 7.58 (s, 1H), 8.46 (bs, 2H) |
| 29 | Me | EtO | Me | 5 | colorless oil | 1.24 (tt, J=8.0, 8.0Hz, 2H), 1.35 (t, J=8.0Hz, 3H), 1.40–1.52 (m, 4H), 2.08 (s, 3H), 2.18 (t, J=8.0Hz, 2H), 2.21 (s, 3H), 2.53 (t, J=8.0Hz, 2H), 3.66 (s, 3H), 3.69 (s, 3H), 3.99 (q, J=8.0Hz, 2H), 7.24 (dd, J=4.8, 7.6Hz, 1H), 7.49 (d, J=7.6Hz, 1H), 7.58 (s, 1H), 8.43 |

TABLE 9-continued

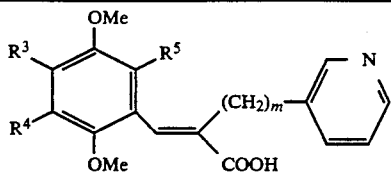

| Ex. No. | $R^3$ | $R^4$ | $R^5$ | n | Properties | $^1$H-NMR spectrum TMS as internal reference, δ value (ppm) |
|---|---|---|---|---|---|---|
| | | | | | | (s, 1H), 8.46 (s, 1H) |

TABLE 10

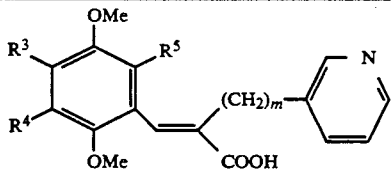

| Ex. No. | $R^3$ | $R^4$ | $R^5$ | n | Properties | $^1$H-NMR spectrum TMS as internal reference, δ value (ppm) |
|---|---|---|---|---|---|---|
| 30 | MeO | Me | Me | 3 | colorless oil | 1.84 (tt, J=7.6, 7.6Hz, 2H), 2.10 (s, 3H), 2.23 (s, 3H), 2.25 (t, J=7.6Hz, 2H), 2.57 (t, J=7.6Hz, 2H), 3.56 (s, 3H), 3.80 (s, 3H), 3.87 (s, 3H), 7.21 (t, J=7.6Hz, 1H), 7.46 (d, J=7.6Hz, 1H), 7.60 (s, 1H), 8.46 (bs, 1H), 8.58 (bs, 1H) |
| 31 | Me | Me | MeO | 5 | colorless oil | 1.30 (tt, J=7.6, 7.6Hz, 2H), 1.42-1.52 (m, 4H), 2.15 (s, 3H), 2.19 (s, 3H), 2.28 (t, J=7.6Hz, 2H), 2.64 (t, J=7.6Hz, 2H), 3.56 (s, 3H), 3.72 (s, 3H), 3.76 (s, 3H), 7.24 (m, 1H), 7.49 (d, J=7.2Hz, 1H), 7.64 (s, 1H), 8.43 (bs, 2H) |
| 32 | MeO | Me | Me | 4 | colorless oil | 1.41-1.58 (m, 4H), 2.08 (s, 3H), 2.18 (s, 3H), 2.25 (t, J=7.2Hz, 2H), 2.53 (t, J=7.2Hz, 2H), 3.55 (s, 3H), 3.78 (s, 3H), 3.85 (s, 3H), 7.21 (t, J=7.6Hz, 1H), 7.44 (d, J=7.6Hz, 1H), 7.59 (s, 1H), 8.44 (bs, 2H) |

TABLE 11

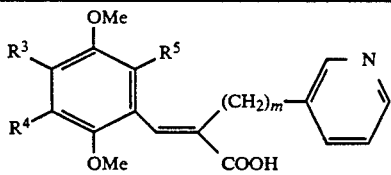

| Ex. No. | $R^3$ | $R^4$ | $R^5$ | n | Properties | $^1$H-NMR spectrum TMS as internal reference, δ value (ppm) |
|---|---|---|---|---|---|---|
| 33 | MeO | Me | Me | 6 | colorless oil | 1.22 (t, J=3.5Hz, 4H), 1.41 (t, J=7.6Hz, 2H), 1.53 (t, J=7.6Hz, 2H), 2.10 (s, 3H), 2.18 (s, 3H), 2.19 (t, J=7.6Hz, 2H), 2.55 (t, J=7.6Hz, 2H), 3.57 (s, 3H), 3.79 (s, 3H), 3.85 (s, 3H), 7.23 (t, J=8.0Hz, 1H), 7.51 (d, J=8.0Hz, 1H), 7.58 (s, 1H), 8.47 (bs, 2H) |
| 34 | Me | MeO | Me | 6 | colorless oil | 1.20-1.27 (m, 4H), 1.42 (tt, J=8.0, 8.0Hz, 2H), 1.55 (tt, J=8.0, 8.0Hz, 2H), 2.11 (s, 3H), 2.19 (t, J=8.0Hz, 2H), 2.23 (s, 3H), 2.58 (t, J=8.0Hz, 3H), 3.69 (s, 3H), 3.71 (s, 3H), 3.82 (s, 3H), 7.26 (d, J=7.6Hz, 1H), 7.54 (d, J=7.6Hz, 1H), 7.58 (s, 1H), 8.50 (bs, 2H) |
| 35 | H | Me | MeO | 5 | colorless oil | 1.28 (t, J=8.0Hz, 2H), 1.30-1.55 (m, 4H), 2.25 (s, 3H), 2.30 (t, J=8.0Hz, 2H), 2.53 (t, J=8.0Hz, 2H), 3.58 (s, 3H), 3.68 (s, 3H), 3.83 (s, 3H), 6.60 (s, 1H), 7.21 (dd, J=5.0, 7.0Hz, 1H), 7.47 (dd, J=1.0, 9.0Hz, 1H), 7.64 (s, 1H), 8.43 (bs, 2H) |

TABLE 12

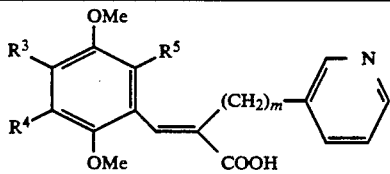

| Ex. No. | $R^3$ | $R^4$ | $R^5$ | n | Properties | $^1$H-NMR spectrum TMS as internal reference, δ value (ppm) |
|---|---|---|---|---|---|---|
| 36 | Me | cyclohexyl-CH$_2$-O | Me | 5 | colorless oil | 1.09 (dq, J=4.0, 12.0Hz, 2H), 1.17-1.34 (m, 4H), 1.42-1.55 (m, 4H), 1.67-1.82 (m, 5H), 1.90 (bd, J=12Hz, 2H), 2.10 (s, 3H), 2.18 (t, J=8.0Hz, 2H), 2.20 (s, 3H), 2.54 (t, J=8.0Hz, 2H), 3.67 (s, 3H), 3.68 (s, 3H), 3.70 (d, J=4.0Hz, 2H), 7.22 (t, J=7.6Hz, 1H), 7.46 (d, J=7.6Hz, 1H), 7.58 (s, 1H), 8.43 (bs, 2H) |

TABLE 12-continued

[Structure: benzene ring with OMe (top), OMe (bottom), R³, R⁴, R⁵ substituents, connected via =CH to C(COOH)-(CH₂)ₘ-3-pyridyl]

| Ex. No. | R³ | R⁴ | R⁵ | n | Properties | ¹H-NMR spectrum TMS as internal reference, δ value (ppm) |
|---|---|---|---|---|---|---|
| 37 | Me | Me | MeO | 4 | colorless oil | 1.46–1.60 (m, 4H), 2.15 (s, 3H), 2.20 (s, 3H), 2.33 (t, J=8.0Hz, 2H), 2.54 (t, J=8.0Hz, 2H), 3.53 (s, 3H), 3.69 (s, 3H), 3.75 (s, 3H), 7.19 (d, J=7.5Hz, 1H), 7.44 (d, J=7.5Hz, 1H), 7.63 (s, 1H), 8.42 (bs, 2H) |
| 38 | EtO | Me | Me | 5 | colorless oil | 1.23 (m, 2H), 1.39 (t, J=7.0Hz, 3H), 1.46 (m, 2H), 1.52 (m, 2H), 2.08 (s, 3H), 2.17 (s, 3H), 2.20 (t, J=8.0Hz, 2H), 2.53 (t, J=8.0Hz, 2H), 3.56 (s, 3H), 3.78 (s, 3H), 4.03 (t, J=7.0Hz, 2H), 7.21 (bs, 1H), 7.46 (d, J=8.0Hz, 1H), 7.58 (s, 1H), 8.43 (bs, 2H) |

TABLE 13

[Same structure as above]

| Ex. No. | R³ | R⁴ | R⁵ | n | Properties | ¹H-NMR spectrum TMS as internal reference, δ value (ppm) |
|---|---|---|---|---|---|---|
| 39 | MeO~~~ | Me | Me | 5 | colorless oil | 1.20 (tt, J=7.5, 7.5Hz, 2H), 1.40–1.55 (m, 4H), 1.74 (tt, J=7.5, 7.5Hz, 2H), 2.11 (s, 3H), 2.18 (t, J=7.5Hz, 3H), 2.24 (s, 3H), 2.51 (t, J=8.0Hz, 2H), 2.66 (t, J=7.5Hz, 2H), 3.34 (s, 3H), 3.41 (t, J=8.0Hz, 2H), 3.57 (s, 3H), 3.64 (s, 3H), 7.22 (dd, J=4.8, 8.0Hz, 1H), 7.47 (d, J=8.0Hz, 1H), 7.62 (s, 1H), 8.44 (bs, 2H) |
| 40 | MeS | Me | Me | 5 | pale-yellow oil | 1.21 (tt, J=7.5, 7.5Hz, 2H), 1.42–1.65 (m, 4H), 2.13 (s, 3H), 2.19 (t, J=7.5Hz, 2H), 2.39 (s, 3H), 2.43 (s, 3H), 2.53 (t, J=7.5Hz, 2H), 3.58 (s, 3H), 3.79 (s, 3H), 7.22 (dd, J=4.5, 7.5Hz, 1H), 7.47 (d, J=7.5Hz, 1H), 7.58 (s, 1H), 8.40–8.51 (m, 2H) |
| 41 | MOMO | Me | Me | 5 | pale-yellow oil | 1.24 (tt, J=7.5, 7.5Hz, 2H), 1.45 (tt, J=7.5, 7.5Hz, 2H), 2.08 (s, 3H), 2.20 (t, J=7.5Hz, 2H), 2.21 (s, 3H), 2.53 (t, J=7.5Hz, 2H), 3.56 (s, 3H), 3.60 (s, 3H), 3.72 (s, 3H), 5.11 (s, 2H), 7.11 (dd, J=4.5, 7.5Hz, 1H), 7.47 (d, J=7.5Hz, 1H), 7.57 (s, 1H), 8.40–8.48 (bs, 2H) |

EXAMPLE 42

(E)-3-(4-Hydroxy-2,5-dimethoxy-3,6-dimethylphenyl)-2-[5-(3-pyridyl)pentyl]-2-propenoic acid

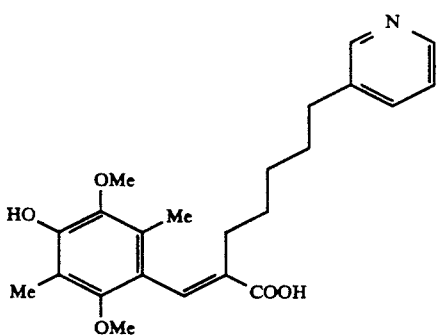

1.85 g of the compound prepared in the Example 41 was dissolved in 15 ml of acetone, followed by the addition of 2.5 ml of concentrated hydrochloric acid. The obtained mixture was stirred at room temperature for 10 hours, neutralized with a saturated aqueous solution of sodium hydrogencarbonate and extracted with ethyl acetate. The organic layer was washed with a saturated aqueous solution of sodium chloride, dried over magnesium sulfate and filtered. The filtrate was distilled to remove the solvent. 7.59 g of the title compound was obtained as a white glassy substance.

¹H-NMR (CDCl₃) δ (ppm); 1.21 (tt, J=7.5, 7.5 Hz, 2H), 1.49 (tt, J=7.5, 7.5 Hz, 2H), 2.12 (s, 3H), 2.17 (s, 3H), 2.02 (t, J=7.5 Hz, 2H), 2.50 (t, J=7.5 Hz, 2H), 3.56 (s, 3H), 3.74 (s, 3H), 7.18–7.28 (m, 1H), 7.24 (d, J=5.5 Hz, 1H), 7.39 (s, 1H), 8.35–8.50 (m, 2H).

EXAMPLE 43

(E)-3-(2-Hydroxy-3,6-dimethyl-1,4-benzoquinon-5-yl)-2-[5-(3-pyridyl)pentyl]-2-propenoic acid hydrochloride

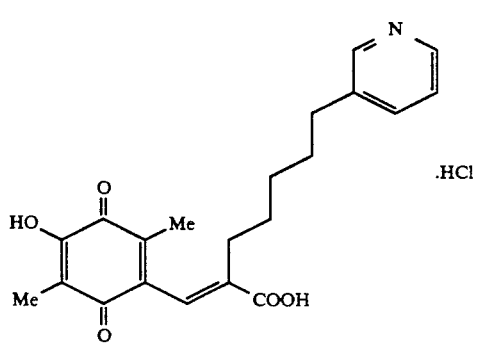

1.26 g of the (E)-3-(4-hydroxy-2,5-dimethoxy-3,6-dimethylphenyl)-2-[5-(3-pyridyl)pentyl]-2-propenoic acid prepared in the Example 42 was dissolved in an acetonitrile (60 ml)/water (30 ml) mixture. The obtained solution was cooled to ice temperature, followed by the gradual dropwise addition of 20 ml of an aqueous solution of 3.63 g of cerium (IV) ammonium nitrate. A 5% aqueous solution of sodium hydrogencarbonate was added to the resulting solution to adjust the pH to 6. The resulting mixture was extracted with ethyl acetate. The organic layer was washed with water, dried over magnesium sulfate and filtered. 1.6 ml of 6N hydrochloric acid and 100 ml of ethanol were added to the filtrate residue was recrystallized from ethanol to give 0.80 g of the title compound as a yellow crystal.

$^1$H-NMR (DMSO-d$_6$) δ (ppm); 1.05–1.18 (m, 2H), 1.20–1.38 (m, 2H), 1.40–1.54 (m, 2H), 1.73 (s, 3H), 1.80 (s, 3H), 2.00 (bt, J=7.0 Hz, 2H), 2.66 (t, J=7.0 Hz, 2H), 7.04 (bs, 1H), 7.91 (dd, J=5.0, 8.0 Hz, 1H), 8.35 (bd, J=8.0 Hz, 1H), 8.65–8.80 (m, 1H), 8.75 (s, 1H).

MS; 370 (MH+).

EXAMPLES 44 TO 62

The compounds listed in the following Tables 14 to 20 were each prepared in a similar manner to that of the Example 3:

TABLE 14

| Ex. No. | R$^3$ | R$^4$ | R$^5$ | n | Properties | $^1$H-NMR spectrum TMS as internal reference, δ value (ppm) |
|---|---|---|---|---|---|---|
| 44 | n-HepO | Me | Me | 5 | yellow oil | 0.76 (t, J=7.0Hz, 3H), 1.20–1.40 (m, 8H), 1.40–1.55 (m, 4H), 1.60 (tt, J=7.0, 7.0Hz, 2H), 1.74 (tt, J=7.0, 7.0Hz, 2H), 1.95 (s, 3H), 1.99 (s, 3H), 2.13 (t, J=7.0Hz, 2H), 2.60 (t, J=7.0Hz, 2H), 4.20 (t, J=7.0Hz, 2H), 7.23 (s, 1H), 7.25 (dd, J=5.0, 8.0Hz, 1H), 7.53 (bd, J=8.0Hz, 1H), 8.43 (d, J=5.0Hz, 1H), 8.49 (bs, 1H) |
| 45 | MeO | Me | Me | 5 | yellow crystal m.p.: 134–135° C. | 1.26 (tt, J=7.0, 7.0Hz, 2H), 1.50 (tt, J=7.0, 7.0Hz, 2H), 1.61 (tt, J=7.0, 7.0Hz, 2H), 1.95 (s, 3H), 1.96 (s, 3H), 2.12 (t, J=7.0Hz, 2H), 2.60 (t, J=7.0Hz, 2H), 4.01 (s, 3H), 7.26 (s, 1H), 7.27 (dd, J=5.0, 8.5Hz, 1H), 7.55 (bd, J=8.5Hz, 1H), 8.44 (bd, J=5.0Hz, 1H), 8.50 (bs, 1H) |
| 46 | Me | MeO | Me | 5 | yellow crystal m.p.: 128–130° C. | 1.27 (tt, J=7.6, 7.6Hz, 2H), 1.51 (tt, J=7.6, 7.6Hz, 2H), 1.61 (tt, J=7.6, 7.6Hz, 2H), 1.97 (s, 3H), 1.98 (s, 3H), 2.13 (t, J=7.2Hz, 2H), 2.61 (t, J=8.0Hz, 2H), 3.98 (s, 3H), 7.23 (s, 1H), 7.28 (dd, J=2.4, 7.2Hz, 1H), 8.45 (d, J=4.8Hz, 1H), 8.90 (s, 1H) |

TABLE 15

| Ex. No. | R$^3$ | R$^4$ | R$^5$ | n | Properties | $^1$H-NMR spectrum TMS as internal reference, δ value (ppm) |
|---|---|---|---|---|---|---|
| 47 | Me | n-BuO | Me | 5 | yellow crystal m.p.: 97–100° C. | 0.95 (t, J=7.4Hz, 3H), 1.26 (tt, J=7.6, 7.6Hz, 2H), 1.40–1.52 (m, 4H), 1.60 (tt, J=7.6, 7.6Hz, 2H), 1.70 (tt, J=7.6, 7.6Hz, 2H), 1.99 (s, 3H), 2.00 (s, 3H), 2.13 (t, J=8.0Hz, 2H), 2.60 (t, J=8.0Hz, 2H), 4.20 (t, J=8.0Hz, 2H), 7.24 (s, 1H), 7.28 (dd, J=2.4, 7.6Hz, 1H), 7.55 (d, J=6.4Hz, 1H), 8.45 (d, J=4.0Hz, 1H), 8.49 (s, 1H) |
| 48 | Me | n-BuO | Me | 3 | yellow crystal m.p.: 92–95° C. | 0.95 (t, J=6.8Hz, 3H), 1.45 (q, J=7.2Hz, 2H), 1.70 (tt, J=4.8, 4.8Hz, 2H), 1.90 (bs, 2H), 1.95 (s, 3H), 1.99 (s, 3H), 2.13–2.27 (m, 2H), 2.53–2.66 (m, 2H), 4.12 (t, J=7.6Hz, 2H), 7.25 (bs, 2H), 7.53 (d, J=6.0Hz, 1H), 8.43 (bs, 1H), 8.61 (bs, 1H) |
| 49 | Me | n-HepO | Me | 5 | yellow oil | 0.87 (t, J=8.0Hz, 3H), 1.22–1.36 (m, 8H), 1.39 (tt, J=7.6, 7.6Hz, 2H), 1.49 (tt, J=7.6, 7.6Hz, 2H), 1.60 (tt, J=7.6, 7.6Hz, 2H), 1.70 (q, J=8.0Hz, 2H), 1.97 (s, 3H), 1.99 (s, 3H), 2.14 (t, J=7.6Hz, 2H), 2.60 (t, J=7.6Hz, 2H), 4.08 (t, J=8.0Hz, 2H), 7.24 (d, J=4.8Hz, 1H), 7.28 (s, 1H), 7.54 (d, J=7.6Hz, 1H), 8.44 (d, J=4.8Hz, 1H), 8.48 (s, 1H) | and the solvent was distilled away in a vacuum. The

TABLE 16

| Ex. No. | R$^3$ | R$^4$ | R$^5$ | n | Properties | $^1$H-NMR spectrum TMS as internal reference, δ value (ppm) |
|---|---|---|---|---|---|---|
| 50 | Me | EtO | Me | 5 | yellow crystal | 1.26 (tt, J=7.6, 7.6Hz, 2H), 1.34 (t, J=6.8Hz, 3H), 1.50 (tt, J=7.6, 7.6Hz, 2H), 1.59 (tt, |

TABLE 16-continued

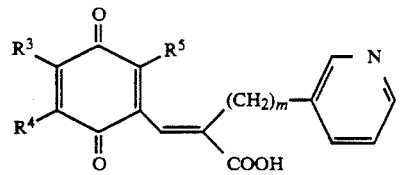

| Ex. No. | R³ | R⁴ | R⁵ | n | Properties | ¹H-NMR spectrum TMS as internal reference, δ value (ppm) |
|---|---|---|---|---|---|---|
| | | | | | m.p.: 105–108° C. | J=7.6, 7.6Hz, 2H), 1.97 (s, 3H), 1.98 (s, 3H), 2.13 (t, J=7.2Hz, 2H), 2.59 (t, J=8.0Hz, 2H), 4.26 (q, J=7.2Hz, 2H), 7.24 (s, 1H), 7.29 (dd, J=2.8, 7.6Hz, 1H), 7.561 (d, J=7.6Hz, 1H), 8.46 (d, J=4.8Hz, 1H), 8.48 (s, 1H) |
| 51 | MeO | Me | Me | 3 | yellow crystal m.p.: 140–142° C. | 1.90 (tt, J=8.0, 8.0Hz, 2H), 1.95 (s, 3H), 1.97 (s, 3H), 2.17 (t, J=8.0Hz, 2H), 2.63 (t, J=8.0Hz, 2H), 4.04 (s, 3H), 7.26 (s, 1H), 7.28 (dd, J=4.5, 7.5Hz, 1H), 7.56 (bd, J=7.5Hz, 1H), 8.47 (bd, J=4.5Hz, 1H), 8.64 (bs, 1H) |
| 52 | Me | Me | MeO | 5 | yellow crystal m.p.: 148–149° C. | 1.28 (tt, J=7.5, 7.5Hz, 2H), 1.51 (tt, J=7.5, 7.5Hz, 2H), 1.60 (tt, J=7.5, 7.5Hz, 2H), 2.03 (s, 3H), 2.04 (s, 3H), 2.18 (t, J=7.5Hz, 2H), 2.59 (t, J=7.5Hz, 2H), 3.96 (s, 3H), 7.27 (dd, J=5.0, 8.0Hz, 1H), 7.30 (s, 1H), 7.55 (bd, J=8.0Hz, 1H), 8.45 (dd, J=1.5, 5.0Hz, 1H), 8.48 (d, J=1.5Hz, 1H) |

TABLE 17

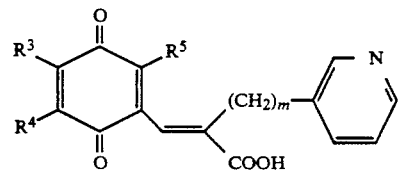

| Ex. No. | R³ | R⁴ | R⁵ | n | Properties | ¹H-NMR spectrum TMS as internal reference, δ value (ppm) |
|---|---|---|---|---|---|---|
| 53 | MeO | Me | Me | 4 | yellow crystal m.p.: 124–125° C. | 1.42–1.63 (m, 4H), 1.95 (s, 6H), 2.17 (t, J=7.0Hz, 2H), 2.62 (t, J=7.0Hz, 2H), 4.03 (s, 3H), 7.25 (s, 1H), 7.31 (dd, J=5.0, 8.0Hz, 1H), 7.60 (d, J=8.0Hz, 1H), 8.46 (bd, J=5.0Hz, 1H), 8.48 (bs, 1H) |
| 54 | MeO | Me | Me | 6 | yellow crystal m.p.: 119–121° C. | 1.15–1.34 (m, 4H), 1.44 (tt, J=7.5, 7.5Hz, 2H), 1.58 (tt, J=7.5, 7.5Hz, 2H), 1.95 (s, 6H), 2.12 (t, J=7.5Hz, 2H), 2.60 (t, J=7.5Hz, 2H), 4.03 (s, 3H), 7.25 (s, 1H), 7.32 (dd, J=5.5, 8.0Hz, 1H), 7.60 (d, J=8.0Hz, 1H), 8.47 (dd, J=1.0, 5.5Hz, 1H), 8.50 (d, J=1.0Hz, 1H) |
| 55 | Me | MeO | Me | 6 | yellow crystal m.p.: 108–110° C. | 1.19–1.33 (m, 4H), 1.45 (tt, J=7.2, 7.2Hz, 2H), 1.58 (tt, J=6.8, 6.8Hz, 2H), 1.97 (s, 3H), 1.98 (s, 3H), 2.13 (t, J=7.6Hz, 2H), 2.60 (t, J=8.0Hz, 2H), 4.99 (s, 3H), 7.24 (d, J=1.2Hz, 1H), 7.29 (dd, J=2.4, 7.2Hz, 1H), 7.57 (d, J=8.0Hz, 1H), 8.46 (d, J=4.8Hz, 1H), 8.49 (s, 1H) |

TABLE 18

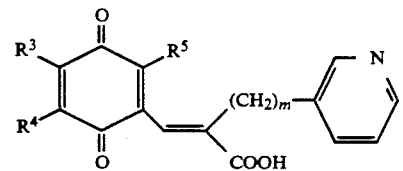

| Ex. No. | R³ | R⁴ | R⁵ | n | Properties | ¹H-NMR spectrum TMS as internal reference, δ value (ppm) |
|---|---|---|---|---|---|---|
| 56 | Me | Me | MeO | 6 | yellow crystal m.p.: 64–66° C. | 1.20–1.31 (m, 4H), 1.43 (tt, J=7.5, 7.5Hz, 2H), 1.56 (tt, J=7.5, 7.5Hz, 2H), 2.01 (s, 3H), 2.03 (s, 3H), 2.15 (t, J=7.5Hz, 2H), 2.55 (t, J=7.5Hz, 2H), 3.94 (s, 3H), 7.25 (t, J=8.0Hz, 1H), 7.27 (s, 1H), 7.53 (d, J=8.0Hz, 1H), 8.46 (bs, 2H) |
| 57 | H | Me | MeO | 5 | yellow crystal m.p.: 110–112° C. | 1.14 (tt, J=8.0, 8.0Hz, 2H), 1.34 (tt, J=8.0, 8.0Hz, 2H), 1.45 (tt, J=8.0, 8.0Hz, 2H), 1.93 (s, 3H), 2.03 (t, J=8.0Hz, 2H), 2.48 (t, J=8.0Hz, 2H), 3.91 (s, 3H), 6.67 (s, 1H), 6.99 (s, 1H), 7.24 (dd, J=4.0, 7.0Hz, 1H), 7.53 (dt, J=1.0, 4.0Hz, 1H), 8.34 (bs, 2H) |
| 58 | Me | Me | Me | 5 | yellow crystal m.p.: 152–154° C. | 1.18–1.31 (m, 2H), 1.40 (m, 4H), 1.97 (s, 3H), 2.03 (s, 3H), 2.05 (s, 3H), 2.12 (t, J=7.2Hz, 2H), 2.60 (t, J=8.0Hz, 2H), 7.22–7.35 (m, 1H), 7.27 (s, 1H), 7.58 (d, J=7.6Hz, 1H), 8.38–8.60 (m, 2H) |

TABLE 19

| Ex. No. | R³ | R⁴ | R⁵ | n | Properties | ¹H-NMR spectrum TMS as internal reference, δ value (ppm) |
|---|---|---|---|---|---|---|
| 59 | Me | cyclohexyl-CH₂-O | Me | 5 | yellow oil | 1.02 (dq, J=4.0, 12.0Hz, 2H), 1.20–1.30 (m, 4H), 1.49 (tt, J=8.0, 8.0Hz, 2H), 1.59 (tt, J=8.0, 8.0Hz, 2H), 1.65–1.85 (m, 7H), 1.95 (s, 3H), 1.98 (s, 3H), 2.12 (t, J=8.0Hz, 2H), 2.59 (t, J=8.0Hz, 2H), 3.99 (d, J=8.0Hz, 2H), 7.23 (s, 1H), 7.27 (d, J=7.2Hz, 1H), 7.53 (d, J=7.2Hz, 1H), 8.45 (bs, 1H), 8.49 (bs, 1H) |
| 60 | Me | Me | MeO | 4 | yellow crystal m.p.: 164–166° C. | 1.36 (tt, J=8.0, 8.0Hz, 2H), 1.46 (tt, J=8.0, 8.0Hz, 2H), 1.92 (s, 3H), 1.96 (s, 3H), 2.09 (t, J=8.0Hz, 2H), 2.50 (t, J=8.0Hz, 2H), 3.86 (s, 3H), 7.01 (s, 1H), 7.25 (dd, J=4.8, 7.6Hz, 1H), 7.52 (d, J=7.6Hz, 1H), 8.33 (s, 1H), 8.35 (d, J=4.8Hz, 1H) |
| 61 | EtO | Me | Me | 5 | yellow crystal m.p.: 116–118° C. | 1.26 (m, 2H), 1.38 (t, J=7.0Hz, 3H), 1.50 (m, 2H), 1.60 (m, 2H), 1.95 (s, 3H), 1.96 (s, 3H), 2.12 (t, J=8.0Hz, 2H), 2.60 (t, J=8.0Hz, 2H), 4.28 (q, J=7.0Hz, 2H), 7.25–7.29 (m, 2H), 7.55 (dt, J=8.0, 1.0Hz, 1H), 8.45 (dd, J=5.0, 1.0Hz, 1H), 8.50 (d, J=1.0Hz, 1H) |

TABLE 20

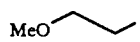

| Ex. No. | R³ | R⁴ | R⁵ | n | Properties | ¹H-NMR spectrum TMS as internal reference, δ value (ppm) |
|---|---|---|---|---|---|---|
| 62 | Me | MeO-CH₂CH₂- | Me | 5 | yellow oil | 1.15 (tt, J=7.5, 7.5Hz, 2H), 1.31 (tt, J=7.5, 7.5Hz, 2H), 1.43–1.58 (m, 4H), 1.83 (s, 3H), 1.96 (s, 3H), 1.99 (t, J=7.5Hz, 2H), 2.43 (t, J=8.0Hz, 2H), 2.67 (t, J=7.5Hz, 2H), 3.16 (s, 3H), 3.24 (t, J=8.0Hz, 2H), 7.05 (s, 1H), 7.93 (t, J=7.5Hz, 1H), 8.35 (d, J=7.5Hz, 1H), 8.72 (bs, 2H) |

EXAMPLE 63

Ethyl 3-(2-methoxy-3,5-dimethyl-1,4-benzoquinon-6-yl)-2-[5-(3-pyridyl)pentyl]propenoate hydrochloride

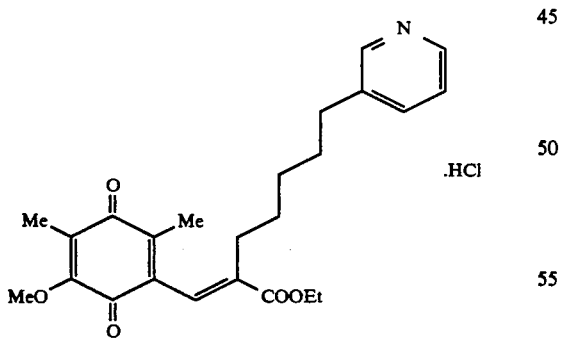

1 g of the compound prepared in the Example 46 was dissolved in 10 ml of ethanol, followed by the addition of 0.7 ml of concentrated sulfuric acid. The obtained mixture was heated under reflux for 12 hours, cooled, neutralized and extracted with ethyl acetate. The organic layer was washed with a saturated aqueous solution of sodium chloride, dried over anhydrous magnesium sulfate and concentrated in a vacuum. The residue was purified by silica gel column chromatography [ethyl acetate (0→30%)/hexane]. The residue was dissolved in a small amount of ethanol, followed by the addition of 0.25 ml of concentrated hydrochloric acid. The obtained mixture was concentrated in a vacuum to give the title compound as a yellow oil.

¹H-NMR (400 MHz, DMSO-d₆) δ (ppm); 1.17 (tt, J=8.0, 8.0 Hz, 2H), 1.27 (t, J=6.4 Hz, 3H), 1.36 (tt, J=8.0, 8.0 Hz, 2H), 1.55 (tt, J=8.0, 8.0 Hz, 2H), 1.85 (s, 3H), 1.88 (s, 3H), 2.07 (t, J=8.0 Hz, 2H), 2.73 (t, J=8.0 Hz, 2H), 3.88 (s, 3H), 4.20 (q, J=6.4 Hz, 2H), 7.06 (s, 1H), 8.00 (dd, J=1.6, 8.0 Hz, 1H), 8.45 (d, J=8.0 Hz, 1H), 8.78 (d, J=5.2 Hz, 1H), 8.81 (s, 1H).

EXAMPLE 64

3-(2-Methoxy-3,5-dimethyl-1,4-benzoquinon-6-yl)-2-[5-(3-pyridyl)pentyl]-1-oxo-1-morpholinyl-2-propene

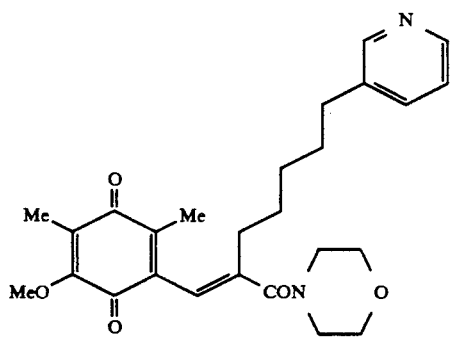

1.4 g of the compound prepared in the Example 46 was dissolved in 200 ml of dichloromethane. The obtained solution was washed with 100 ml of a 10% aqueous solution of sodium hydrosulfite twice. The dichloromethane layer was dried over anhydrous magnesium sulfate and concentrated in a vacuum. 20 ml of N,N-dimethylformamide and 1 g of sodium hydrosulfite were added to the residue. The obtained mixture was cooled to 0° C., followed by the dropwise addition of 1.1 g of diphenylphosphorylazide, 0.32 g of morpholine and 0.38 g of triethylamine in this order. The obtained mixture was stirred at room temperature day and night, followed by the addition of water. The obtained mixture was extracted with ethyl acetate. The organic layer was stirred while bubbling air thereinto for 2 hours, washed with a saturated aqueous solution of sodium chloride, dried over anhydrous magnesium sulfate and concentrated in a vacuum. The residue was purified by silica gel column chromatography (ethyl acetate) to give 0.71 g of the title compound as an orange oil.

$^1$H-NMR (400 MHz, CDCl$_3$) δ (ppm); 1.27 (tt, J=8.0, 8.0 Hz, 2H), 1.36 (tt, J=8.0, 8.0 Hz, 2H), 1.55 (tt, J=8.0, 8.0 Hz, 2H), 1.98 (s, 6H), 2.10 (t, J=8.0 Hz, 2H), 2.55 (t, J=8.0 Hz, 2H), 3.65–3.80 (m, 8H), 3.96 (s, 3H), 5.97 (d, J=1.2 Hz, 1H), 7.18 (dd, J=3.6, 8.0 Hz, 1H), 7.44 (dt, J=1.2, 8.0 Hz, 1H), 8.39 (d, J=1.5 Hz, 1H), 8.42 (dd, J=1.5, 3.6 Hz, 1H).

TOXICITY TEST (1)

Repetitive Oral Administration Test for 4 Weeks on Rats

Method 30 and 100 mg/kg of the compound obtained in the Example 3 was orally administered to female Slc:SD rats aged 7 weeks (each group consisting of 5 animals) for 4 weeks. This compound was suspended in a 0.5 wt. % aqueous solution of methylcellulose and administered once a day.

During the administration period, the general conditions of the animals were observed and the body weight and feed intake were measured. After the completion of the final administration, hematological examination, hemo-biochemical examination, urinalysis and autopsy were effected and organs were weighed. Further, livers and kidneys were patho-histologically examined under an optical microscope.

Results

No change was observed at each of the doses of 30 and 100 mg/kg.

TOXICITY TEST (2)

Repetitive Oral Administration Test for 4 Weeks on Dogs

Method 30 and 100 mg/kg of the compound obtained in the Example 3 was orally administered to female beagles aged 8 months (each group consisting of 2 animals) for 4 weeks. This compound was triturated with lactose and administered once a day.

During the administration period, the general conditions of the animals were observed and the body weight and feed intake were measured. After the completion of the first, seventh and final administrations, hemo-biochemical examination was effected. After the completion of the seventh and final administrations, further, hematological examination and urinalysis were effected. Furthermore, autopsy was effected and organs were weighed after the final administration. Livers, kidneys and adrenal bodies were patho-histologically examined under an optical microscope.

Results

No change was observed at each of the doses of 30 and 100 mg/kg.

Thus the toxicologically non-influential dose of the compound obtained in the Example 3 was judged to be 100 mg/kg.

What we claim is:

1. A quinone derivative represented by the following general formula (I) or a pharmacologically acceptable salt thereof:

wherein A stands for a group represented by the formula:

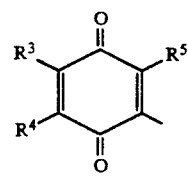

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group, or a group represented by the formula:

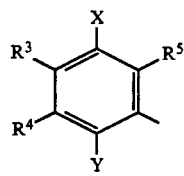

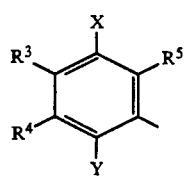

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group; X and Y are the same or different from each other and each stand for a hydroxyl group or a protected hydroxyl group; $R^1$ stands for a heteroarylalkyl group selected from the group consisting of a pyridylalkyl group and an imidazolylalkyl group; and B stands for a carboxyl group or a protected carboxyl group.

2. Leukotrienes production inhibitor comprising a quinone derivative or pharmacologically acceptable salt thereof as set forth in claim 1 as an active ingredient.

3. Thromboxanes production inhibitor comprising a quinone derivative or pharmacologically acceptable salt thereof as set forth in claim 1 as an active ingredient.

4. A therapeutic agent for treating diseases for which leukotrienes production inhibitor is efficacious, which comprises a quinone derivative or pharmacologically acceptable salt thereof as set forth in claim 1 as an active ingredient.

5. A therapeutic agent for treating diseases for which thromboxanes inhibitor is efficacious, which comprises a quinone derivative or pharmacologically acceptable salt thereof as set forth in claim 1 as an active ingredient.

6. A pharmacological composition which comprises a therapeutically effective amount of the quinone derivative or a pharmacologically acceptable salt thereof as set forth in claim 1 and a pharmacologically acceptable vehicle.

7. A method of using a quinone derivative or a pharmacologically acceptable salt thereof as set forth in claim 1 comprising the step of making a medicament containing said quinone derivative as an active ingredient for treating a disease in which the production of leukotriene is elevated.

8. A method of using a quinone derivative or a pharmacologically acceptable salt thereof as set forth in claim 1 comprising the step of making a medicament containing said quinone derivative as an active ingredient for treating a disease in which the production of thromboxane $A_2$ is elevated.

9. A method for treating a disease which comprises administering a pharmaceutically effective amount of the quinone derivative or pharmacologically acceptable salt thereof as set forth in claim 1 to a patient suffering from a disease in which the production of leukotriene is elevated.

10. A method for treating a disease which comprises administering a pharmaceutically effective amount of the quinone derivative or pharmacologically acceptable salt thereof as set forth in claim 1 to a patient suffering from a disease in which the production of thromboxane $A_2$ is elevated.

11. A method for treating a disease which comprises administering a pharmaceutically effective amount of the quinone derivative or pharmacologically acceptable salt thereof as set forth in claim 1 to a patient suffering from a disease selected from the group consisting of asthma, myocardial infarction, angina pectoris, cerebral embolism, cerebral thrombosis, renal insufficiency, nephrosis and nephritis.

12. A quinone derivative or pharmacologically acceptable salt thereof as claimed in claim 1, wherein $R^3$ is a lower alkoxy group.

13. A quinone derivative or pharmacologically acceptable salt thereof as claimed in claim 1, wherein $R^4$ is a lower alkyl group.

14. A quinone derivative or pharmacologically acceptable salt thereof as claimed in claim 1, wherein $R^5$ is a lower alkyl group.

15. A quinone derivative or pharmacologically acceptable salt thereof as claimed in claim 1, wherein X is a hydroxy group or a alkoxy group.

16. A quinone derivative or pharmacologically acceptable salt thereof as claimed in claim 1, wherein Y is a hydroxy group or a alkoxy group.

17. A quinone derivative or pharmacologically acceptable salt thereof as claimed in claim 1, wherein B is a carboxyl group.

18. A quinone derivative or pharmacologically acceptable salt thereof as claimed in claim 1, wherein $R^3$ is a methoxy group or a methyl group.

19. A quinone derivative or pharmacologically acceptable salt thereof as claimed in claim 1, wherein $R^4$ is a methyl group or a methoxy group.

20. A quinone derivative or pharmacologically acceptable salt thereof as claimed in claim 1, wherein $R^5$ is a methyl group or a methoxy group.

21. A quinone derivative or pharmacologically acceptable salt thereof as claimed in claim 1, wherein X is a hydroxy group or a methoxy group.

22. A quinone derivative or pharmacologically acceptable salt thereof as claimed in claim 1, wherein Y is a hydroxy group or a methoxy group.

23. A quinone derivative represented by the following general formula (I) or a pharmacologically acceptable salt thereof:

wherein A stands for a group represented by the formula:

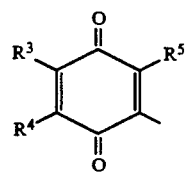

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group, or a group represented by the formula:

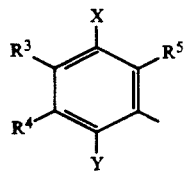

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group; X and Y are the same or different from each other and each stand for a hydroxyl group or a protected hydroxyl group $R^1$ stands for a 5 or 6 membered nitrogen-containing heteroarylalkyl group selected from the group consisting of a pyridylalkyl group and an imidazolylalkyl group; and B stands for a carboxyl group or a protected carboxyl group.

24. A quinone derivative or pharmacologically acceptable salt thereof as claimed in claim 23, wherein $R^1$ is an imidazolylalkyl group.

25. A quinone derivative represented by the following general formula (I) or a pharmacologically acceptable salt thereof:

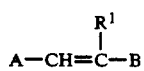

wherein A stands for a group represented by the formula:

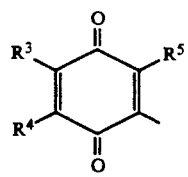

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group, or a group represented by the formula:

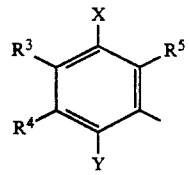

wherein $R^3$, $R^4$ and $R^5$ are the same or different from each other and each stand for a hydrogen atom, a hydroxyl group, a lower alkyl group, a lower alkoxy group, an alkoxyalkyl group, an alkoxyalkoxy group, a cycloalkylalkoxy group, a thiol group or a thioalkyl group, with the proviso that $R^3$ and $R^4$ are not simultaneously each a lower alkoxy group; X and Y are the same or different from each other and each stand for a hydroxyl group or a protected hydroxyl group; $R^1$ is a pyridylhexyl group or a pyridylpentyl group; and B stands for a carboxyl group or a protected carboxyl group.

26. A quinone derivative or pharmacologically acceptable salt thereof wherein the quinone derivative is selected from the group consisting of the below listed quinone derivatives:

(E)-3-(2-Methoxy-3,5-dimethyl-1,4-benzoquinon-6-yl)-2-[5-(3-pyridyl)pentyl]-2-propenoic acid (E)-3-(2-Methoxy-5,6-dimethyl-1,4-benzoquinon-3-yl)-2-[5-(3-pyridyl)pentyl]-2-propenoic acid (E)-3-(2-Methoxy-5,6-dimethyl-1,4-benzoquinon-3-yl)-2-[6-(3-pyridyl)hexyl]-2-propenoic acid (E)-3-(2,4,5-Trimethoxy-3,6-dimethylphenyl)-2-[5-(3-pyridyl)pentyl]-2-propenoic acid (E)-3-(2,5-Dihydroxy-4-methoxy-3,6-dimethylphenyl)-2-[5-(3-pyridyl)pentyl]-2-propenoic acid (E)-3-(2,3,5-Trimethoxy-4,6-dimethylphenyl)-2-[5-(3-pyridyl)pentyl]-2-propenoic acid.

27. A quinone derivative or pharmacologically acceptable salt thereof wherein the quinone derivative is (E)-3-(2-methoxy-3,6-dimethyl-1,4-benzoquinon-5-yl)-2-[5-(3-pyridyl)pentyl]-2-propenoic acid.

28. A quinone derivative represented by the following general formula (I) or a pharmacologically acceptable salt thereof:

wherein A stands for a group represented by the formula:

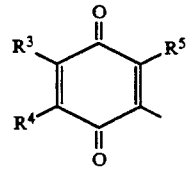

wherein $R^3$, $R^4$ and $R^5$ are the same or different from each other and each stand for a hydrogen atom, a hydroxyl group, a lower alkyl group, a lower alkoxy group, an alkoxyalkyl group, a cycloalkylalkoxy group, a thiol group or a thioalkyl group, with the proviso that $R^3$ and $R^4$ are not simultaneous each a lower alkoxy group, or a group represented by the formula:

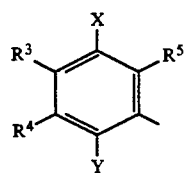

wherein $R^3$, $R^4$ and $R^5$ are the same or different from each other and each stand for a hydrogen atom, a hydroxyl group, a lower alkyl group, a lower alkoxy group, an alkoxyalkyl group, a cycloalkylalkoxy group, a thiol group or a thioalkyl group, with the proviso that $R^3$ and $R^4$ are not simultaneously each a lower alkoxy group; X and Y are the same or different from each other and each stands for a hydroxyl group or a protected hydroxyl group; $R^1$ is a pyridylalkyl group; and B stands for a carboxyl group or a protected carboxyl group.

* * * * *

UNITED STATES PATENT AND TRADEMARK OFFICE
CERTIFICATE OF CORRECTION

PATENT NO. : 5,329,010

DATED : July 12, 1994

INVENTOR(S): Yasushi OKAMOTO et al

It is certified that error appears in the above-indentified patent and that said Letters Patent is hereby corrected as shown below:

Column 37, line 30; after "group" insert ---;---.

Signed and Sealed this

Eighteenth Day of October, 1994

Attest:

BRUCE LEHMAN

Attesting Officer

Commissioner of Patents and Trademarks